(12) United States Patent
Aoyama

(10) Patent No.: US 12,171,397 B2
(45) Date of Patent: Dec. 24, 2024

(54) ENDOSCOPE SYSTEM AND METHOD OF OPERATING THE SAME

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 443 days.

(21) Appl. No.: 17/715,925

(22) Filed: Apr. 7, 2022

(65) Prior Publication Data

US 2022/0225866 A1    Jul. 21, 2022

Related U.S. Application Data

(63) Continuation of application No. PCT/JP2020/036988, filed on Sep. 29, 2020.

(30) Foreign Application Priority Data

Oct. 10, 2019    (JP) .................... 2019-186736

(51) Int. Cl.
    *A61B 1/00*      (2006.01)
    *A61B 1/045*      (2006.01)
    (Continued)

(52) U.S. Cl.
    CPC .... *A61B 1/000094* (2022.02); *A61B 1/00045* (2013.01); *A61B 1/045* (2013.01);
    (Continued)

(58) Field of Classification Search
None
See application file for complete search history.

(56) References Cited

U.S. PATENT DOCUMENTS 9,629,527 B2    4/2017    Kaku et al.
9,649,018 B2    5/2017    Morimoto et al.
(Continued)

FOREIGN PATENT DOCUMENTS

CN    103997946    8/2014
CN    104023618    9/2014
(Continued)

OTHER PUBLICATIONS

"International Search Report (Form PCT/ISA/210) of PCT/JP2020/036988," mailed on Nov. 17, 2020, with English translation thereof, pp. 1-5.
(Continued)

*Primary Examiner* — John P Leubecker
*Assistant Examiner* — Jae Woo
(74) *Attorney, Agent, or Firm* — JCIPRNET

(57) ABSTRACT

Violet light and green light are mixed and emitted at a first light amount ratio. A contrast difference value $\Delta C1$ of first mixed color light emission between a blood vessel contrast of a blue image of first mixed color light emission and a blood vessel contrast of a green image of first mixed color light emission at a specific blood vessel depth satisfies a first condition, and a cross-point blood vessel depth $VD1$ of first mixed color light emission corresponding to a cross-point $CP1$ between the blood vessel contrast of the blue image of the first mixed color light emission and the blood vessel contrast of the green image of the first mixed color light emission satisfies a second condition.

13 Claims, 19 Drawing Sheets

(51) Int. Cl.
  *A61B 1/06* (2006.01)
  *A61B 5/00* (2006.01)
  *G06T 7/00* (2017.01)
  *G06T 7/55* (2017.01)
  *G06T 7/90* (2017.01)
  *H04N 23/12* (2023.01)
  *H04N 23/74* (2023.01)
  *H04N 23/50* (2023.01)

(52) U.S. Cl.
  CPC .............. *A61B 1/06* (2013.01); *A61B 1/0638* (2013.01); *A61B 5/4842* (2013.01); *G06T 7/0012* (2013.01); *G06T 7/55* (2017.01); *G06T 7/90* (2017.01); *H04N 23/12* (2023.01); *H04N 23/74* (2023.01); *G06T 2207/10024* (2013.01); *G06T 2207/10068* (2013.01); *G06T 2207/10152* (2013.01); *G06T 2207/30101* (2013.01); *H04N 23/555* (2023.01)

(56) References Cited

U.S. PATENT DOCUMENTS

| | | | |
|---|---|---|---|
| 9,943,230 | B2 | 4/2018 | Kaku et al. |
| 9,962,070 | B2* | 5/2018 | Terakawa .............. A61B 1/0638 |
| 10,039,439 | B2* | 8/2018 | Aoyama ................. H04N 23/56 |
| 2015/0094538 | A1* | 4/2015 | Terakawa .............. A61B 1/0638 |
| | | | 600/160 |
| 2016/0089010 | A1* | 3/2016 | Aoyama .............. A61B 1/0005 |
| | | | 348/70 |
| 2016/0089011 | A1* | 3/2016 | Shiraishi .............. H04N 23/843 |
| | | | 348/71 |
| 2016/0089012 | A1* | 3/2016 | Aoyama ................ H04N 23/74 |
| | | | 348/71 |
| 2017/0014021 | A1 | 1/2017 | Kuramoto |
| 2018/0214009 | A1* | 8/2018 | Endo ...................... A61B 1/063 |
| 2018/0249889 | A1* | 9/2018 | Imai ..................... A61B 1/0655 |
| 2018/0289240 | A1* | 10/2018 | Aoyama .......... A61B 1/000094 |
| 2020/0170492 | A1* | 6/2020 | Kuramoto ............. A61B 5/489 |
| 2021/0161372 | A1* | 6/2021 | Iwane .............. A61B 1/000094 |
| 2022/0225866 | A1* | 7/2022 | Aoyama ............... G06T 7/0012 |

FOREIGN PATENT DOCUMENTS

| | | |
|---|---|---|
| CN | 104274146 | 1/2015 |
| CN | 106163372 | 11/2016 |
| JP | 2016067775 | 5/2016 |
| JP | 2016067780 | 5/2016 |
| JP | 6153912 | 6/2017 |
| JP | 6196598 | 9/2017 |
| JP | 2017202241 | 11/2017 |
| JP | 2019122865 | 7/2019 |

OTHER PUBLICATIONS

"Written Opinion of the International Searching Authority (Form PCT/ISA/237)" of PCT/JP2020/036988, mailed on Nov. 17, 2020, with English translation thereof, pp. 1-12.

"Notice of Reasons for Refusal of Japan Counterpart Application", issued on Mar. 14, 2023, with English translation thereof, p. 1-p. 21.

"Office Action of China Counterpart Application", issued on Aug. 29, 2024, with English translation thereof, pp. 1-34.

* cited by examiner

FIG. 14

| | Vs | Bs | Gs | Rs | B0 | G0 | CONTRAST DIFFERENCE VALUE | CROSS-POINT BLOOD VESSEL DEPTH |
|---|---|---|---|---|---|---|---|---|
| EXAMPLE 1 | 1.0 | 0 | 0.45 | 0.0 | 0.261 | 0.346 | 0.085 | 55 μm |
| EXAMPLE 2 | 1.0 | 0 | 0.3 | 0.0 | 0.236 | 0.338 | 0.102 | 55 μm |
| EXAMPLE 3 | 1.0 | 0 | 0.15 | 0.0 | 0.200 | 0.317 | 0.117 | 60 μm |
| EXAMPLE 4 | 1.0 | 0 | 0.45 | 0.15 | 0.278 | 0.393 | 0.115 | 75 μm |
| EXAMPLE 5 | 1.0 | 0 | 0.3 | 0.1 | 0.250 | 0.384 | 0.134 | 75 μm |
| EXAMPLE 6 | 1.0 | 0 | 0.15 | 0.05 | 0.209 | 0.359 | 0.150 | 75 μm |
| COMPARATIVE EXAMPLE 1 | 1.0 | 0 | 0.15 | 0.15 | 0.226 | 0.428 | 0.202 | 100 μm |
| COMPARATIVE EXAMPLE 2 | 1.0 | 0 | 0.15 | 0.1 | 0.218 | 0.396 | 0.178 | 90 μm |
| COMPARATIVE EXAMPLE 3 | 1.0 | 0.3 | 0.45 | 0.15 | 0.284 | 0.383 | 0.099 | 85 μm |
| COMPARATIVE EXAMPLE 4 | 1.0 | 0.2 | 0.3 | 0.1 | 0.265 | 0.375 | 0.110 | 85 μm |
| COMPARATIVE EXAMPLE 5 | 1.0 | 0.1 | 0.15 | 0.05 | 0.231 | 0.354 | 0.123 | 85 μm |
| | Vs | Bs | Gs | Rs | B0m | G0m | ΔCm | CPm |
| MONOCHROMATIC V, B LIGHT EMISSION | 1.0 | 0.5 | 0 | 0 | 0.146 | 0.293 | 0.147 | 60 μm |

EXAMPLE 1 (BLOOD VESSEL IMAGE)

FIG. 17  MONOCHROMATIC V, B LIGHT EMISSION

EXAMPLE 1 (DIFFERENCE DISPLAY IMAGE)

FIG. 19 EXAMPLE 3 (BLOOD VESSEL IMAGE)

FIG. 20 EXAMPLE 4 (BLOOD VESSEL IMAGE)

FIG. 21 EXAMPLE 4 (DIFFERENCE DISPLAY IMAGE)

EXAMPLE 6 (BLOOD VESSEL IMAGE)

COMPARATIVE EXAMPLE 1
(BLOOD VESSEL IMAGE)

ENDOSCOPE SYSTEM AND METHOD OF OPERATING THE SAME

CROSS-REFERENCE TO RELATED APPLICATIONS

This application is a Continuation of PCT International Application No. PCT/JP2020/036988 filed on 29 Sep. 2020, which claims priority under 35 U.S.C. § 119(a) to Japanese Patent Application No. 2019-186736 filed on 10 Oct. 2019. The above application is hereby expressly incorporated by reference, in its entirety, into the present application.

BACKGROUND OF THE INVENTION

1. Field of the Invention

The present invention relates to an endoscope system that displays a plurality of blood vessels having depths different from each other and a method of operating the endoscope system.

2. Description of the Related Art

In a medical field, a diagnosis is widely made using a medical image. For example, there is an endoscope system that comprises a light source device, an endoscope, and a processor device as an apparatus using a medical image. In the endoscope system, an object to be observed is irradiated with illumination light and an endoscopic image as a medical image is acquired from the image pickup of the object to be observed illuminated with the illumination light. The endoscopic image is displayed on a display and is used for diagnosis.

Further, in recent years, a disease has been determined using features appearing in an endoscopic image. For example, since a change in the blood vessel density of an extremely superficial layer is significantly increased with the progress of the stage of Barrett's esophagus that is one of diseases, a user determines the stage of Barrett's esophagus while focusing on the blood vessels of the extremely superficial layer. Accordingly, a technique for extracting blood vessels having a specific depth, such as extremely superficial blood vessels, is required in order to reliably perform the determination of a disease, such as the determination of the stage of Barrett's esophagus. On the other hand, in JP2016-067775A (corresponding to US2016/089010A1), JP6196598B, and JP6153912B, violet light having a central wavelength of 410 nm and blue light having a central wavelength of 450 nm are alternately emitted and information about blood vessels of an extremely superficial layer is visualized on the basis of signals obtained from specific pixels of an image pickup sensor at the time of emission of each of the violet light and the blue light. Usually, the image pickup sensor is a color sensor consisting of three types of pixels of R, G, and B, and blue light having a central wavelength of 450 nm become signals obtained from B pixels.

The reason why the violet light and the blue light described above are to be used is as follows. It is known that, in the case of the violet light having a central wavelength of 410 nm, the contrast of shallow blood vessels is high but the contrast of the blood vessels is rapidly reduced with an increase in blood vessel depth. On the other hand, it is known that, in the case of the blue light having a central wavelength of 450 nm, the contrast of shallow blood vessels is lower than that in the case of the violet light having a central wavelength of 410 nm but a reduction in the contrast of the blood vessels depending on an increase in blood vessel depth is gradual. Since the violet light and the blue light having different changes in the contrast of the blood vessels described above are used, information about the blood vessels of the extremely superficial blood vessel can be visualized.

SUMMARY OF THE INVENTION

However, since both the violet light and the blue light are signals to be obtained from the B pixels of the image pickup sensor, it is not possible to simultaneously acquire signals caused by the violet light and the blue light. For this reason, in JP2016-067775A, JP6196598B, and JP6153912B, the violet light and the blue light are alternately emitted to acquire signals corresponding to the emission of each of the violet light and the blue light. Since the violet light and the blue light are alternately emitted, the image pickup times of the violet light and the blue light deviate from each other. On the other hand, the image of the violet light and the image of the blue light are aligned with each other and processing for improving robustness is performed as in JP6153912B to solve a problem caused by a deviation in image pickup time. However, alignment processing or processing for improving robustness increases the processing load of a processor device. Further, it might be difficult to acquire accurate information about blood vessels of the extremely superficial layer.

Accordingly, in order to visualize extremely superficial blood vessels or the like with no positional deviation, it is conceivable to mix two types of illumination light having different wavelengths, such as violet light and green light, and simultaneously emit the two types of illumination light. In this case, it is necessary to set the light amount ratio of the two types of illumination light so that the same visibility as visibility that is obtained in a case where the two types of illumination light are alternately emitted is obtained. In this regard, JP2019-122865A discloses that, in a case where violet light and blue light for exciting green light or red light from a phosphor are simultaneously emitted, the light amount ratio of the violet light and blue light is set so that the contrast of blood vessels with respect to a mucous membrane becomes a target contrast corresponding to the depth and thickness of the blood vessels. However, JP2019-122865A does not disclose and suggest the light amount ratio of two types of illumination light that are used to clarify a difference between extremely superficial blood vessels and superficial blood vessels positioned at a position deeper than the extremely superficial blood vessels.

An object of the present invention is to provide an endoscope system that can clarify a difference between a plurality of blood vessels having depths different from each other in a case where a plurality of types of illumination light having wavelengths different from each other are mixed and applied to an object to be observed, and a method of operating the endoscope system.

An endoscope system according to an aspect of the present invention comprises: a light source unit that emits violet light and green light; a light source processor that allows the violet light and the green light to be independently emitted and allows the violet light and the green light to be mixed and emitted at a first light amount ratio; and an image control processor acquiring a color image of first mixed color light emission that is obtained from image pickup of an object to be observed, to which the violet light and the green light are emitted at the first light amount ratio, and includes a blue image including a component of the violet light and a green image including a component of the green light. A contrast difference value of first mixed color light emission between a blood vessel contrast of the blue image of the first mixed color light emission and a blood vessel contrast of the green image of the first mixed color light emission at a specific blood vessel depth satisfies a first condition, and a cross-point blood vessel depth of first mixed color light emission corresponding to a cross-point between the blood vessel contrast of the blue image of the first mixed color light emission and the blood vessel contrast of the green image of the first mixed color light emission satisfies a second condition.

It is preferable that the first condition is that the contrast difference value of the first mixed color light emission is in a first range determined on the basis of a contrast difference value of monochromatic light emission between a blood vessel contrast of a blue image of monochromatic violet light emission, which is obtained in a case where only the violet light is emitted at the specific blood vessel depth, and a blood vessel contrast of a blue image of monochromatic blue light emission which is obtained in a case where only blue light is emitted.

It is preferable that the second condition is that the cross-point blood vessel depth of the first mixed color light emission is in a second range determined on the basis of a cross-point blood vessel depth of monochromatic light emission corresponding to a cross-point between a blood vessel contrast of a blue image of monochromatic violet light emission, which is obtained in a case where only the violet light is emitted, and a blood vessel contrast of a blue image of monochromatic blue light emission which is obtained in a case where only blue light is emitted.

An endoscope system according to another aspect of the present invention comprises: a light source unit that emits violet light, green light, and red light; a light source processor that allows the violet light, the green light, and the red light to be independently emitted and allows the violet light, the green light, and the red light to be mixed and emitted at a second light amount ratio; and an image control processor acquiring a color image of second mixed color light emission that is obtained from image pickup of an object to be observed, to which the violet light, the green light, and the red light are emitted at the second light amount ratio, and includes a blue image including a component of the violet light and a green image including components of the green light and the red light. A contrast difference value of second mixed color light emission between a blood vessel contrast of the blue image of the second mixed color light emission and a blood vessel contrast of the green image of the second mixed color light emission at a specific blood vessel depth satisfies a first condition, and a cross-point blood vessel depth of second mixed color light emission corresponding to a cross-point between the blood vessel contrast of the blue image of the second mixed color light emission and the blood vessel contrast of the green image of the second mixed color light emission satisfies a second condition.

It is preferable that the image control processor performs image processing for blood vessels, which increases a difference in visibility between a plurality of blood vessels having blood vessel depths different from each other, on the color image of the first mixed color light emission. It is preferable that the image control processor performs image processing for blood vessels, which increases a difference in visibility between a plurality of blood vessels having blood vessel depths different from each other, on the color image of the second mixed color light emission. It is preferable that the image control processor calculates an index value related to a stage of a disease or determines the stage of the disease on the basis of the color image.

It is preferable that the image control processor displays a blood vessel image, which is obtained in a case where the blue image is assigned to luminance signals and calculation images based on the blue image and the green image are assigned to color difference signals, on a display. It is preferable that the image control processor separates and extracts a plurality of blood vessels, which have blood vessel depths different from each other, on the basis of the color image. It is preferable that a central wavelength of the violet light includes a wavelength of 405 nm and a wavelength range of the green light includes a wavelength of 480 to 600 nm. It is preferable that a central wavelength of the violet light includes a wavelength of 405 nm, a wavelength range of the green light includes a wavelength of 480 to 600 nm, and a central wavelength of the red light includes a wavelength of 620 to 630 nm.

A method of operating an endoscope system according to still another aspect of the present invention comprises: a step of causing a light source processor, which controls a light source unit that emits violet light and green light, to allow the violet light and the green light to be independently emitted and to allow the violet light and the green light to be mixed and emitted at a first light amount ratio; and a step of acquiring a color image of first mixed color light emission that is obtained from image pickup of an object to be observed, to which the violet light and the green light are emitted at the first light amount ratio, and includes a blue image including a component of the violet light and a green image including a component of the green light. A contrast difference value of first mixed color light emission between a blood vessel contrast of the blue image of the first mixed color light emission and a blood vessel contrast of the green image of the first mixed color light emission at a specific blood vessel depth satisfies a first condition, and a cross-point blood vessel depth of first mixed color light emission corresponding to a cross-point between the blood vessel contrast of the blue image of the first mixed color light emission and the blood vessel contrast of the green image of the first mixed color light emission satisfies a second condition.

According to the present invention, it is possible to clarify a difference between a plurality of blood vessels having depths different from each other in a case where a plurality of types of illumination light having wavelengths different from each other are mixed and applied to an object to be observed.

BRIEF DESCRIPTION OF THE DRAWINGS

FIG. 14 is a table showing light amount ratios, contrast difference values, and cross-point blood vessel depths of Examples 1 to 6 and Comparative examples 1 to 5.

DESCRIPTION OF THE PREFERRED EMBODIMENTS

Figure 1:
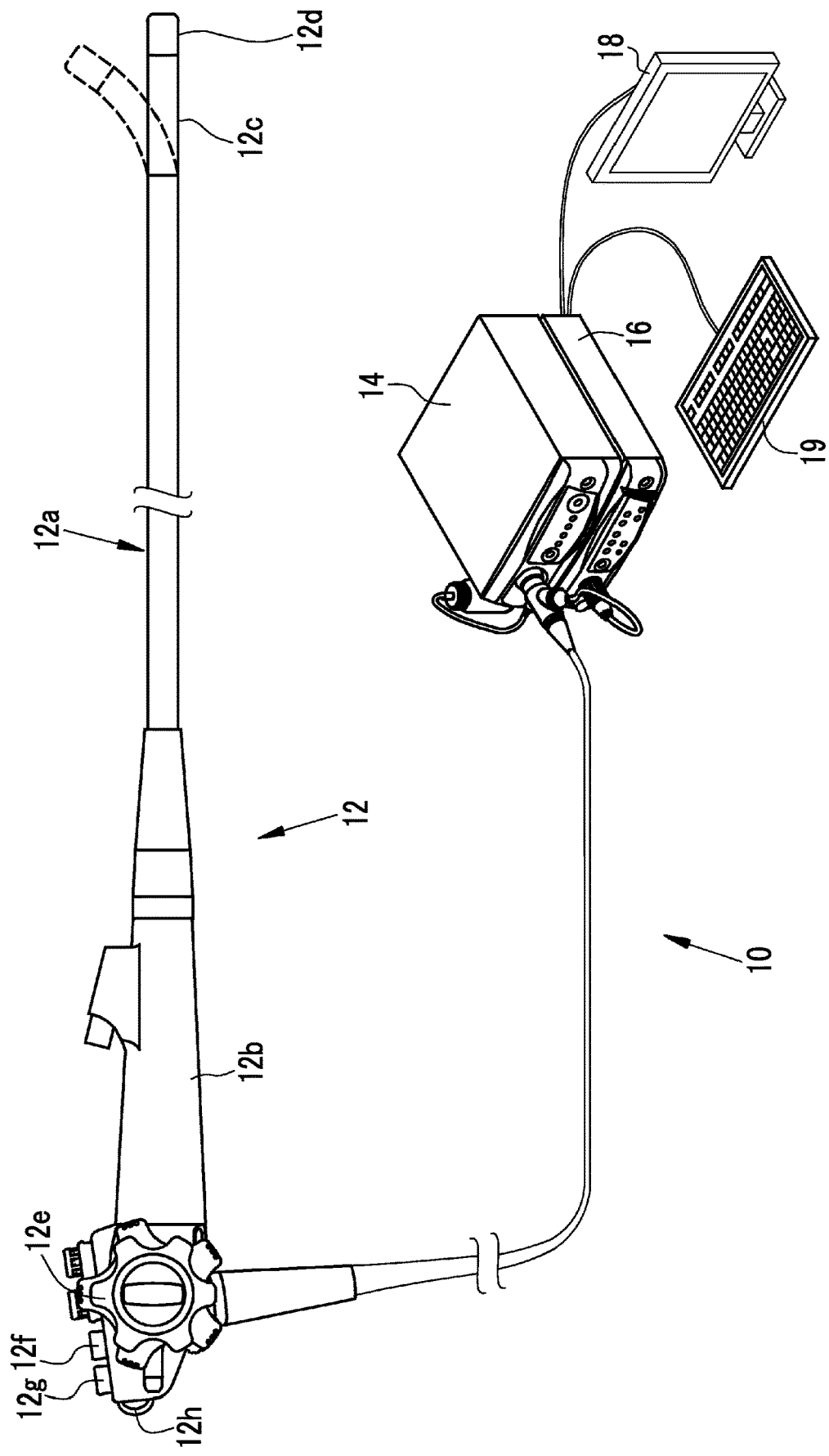
FIG. 1 is a diagram showing the appearance of an endoscope system.

In FIG. 1, an endoscope system 10 comprises an endoscope 12, a light source device 14, a processor device 16, a display 18, and a user interface 19. The endoscope 12 is optically connected to the light source device 14, and is electrically connected to the processor device 16. The endoscope 12 includes an insertion part 12a that is to be inserted into the body of an object to be observed, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d is made to face in a desired direction.

Further, the operation part 12b is provided with a mode changeover switch (SW) 12f that is used for an operation for switching a mode, a static image-acquisition instruction part 12g that is used for an instruction to acquire the static image of the object to be observed, and a zoom operation part 12h that is used for the operation of a zoom lens 43 (see FIG. 2), in addition to the angle knobs 12e.

The endoscope system 10 has three modes, that is, a normal light mode, a special light mode, and a disease-related processing mode. In the normal light mode, the object to be observed is illuminated with normal light and the image of the object to be observed is picked up, so that a normal light image having a natural hue is displayed on the display 18. In the special light mode, the object to be observed is illuminated with special light having a wavelength range different from the wavelength range of normal light and the image of the object to be observed is picked up, so that a special light image in which a specific structure is enhanced is displayed on the monitor 18. In the disease-related processing mode, the stage of Barrett's esophagus, which is one of diseases, is determined on the basis of the normal light image or the special light image. In the disease-related treatment mode, treatment for other diseases, such as whether or not ulcerative colitis has pathologically remitted, may be performed in addition to Barrett's esophagus.

The special light image (endoscopic image) is used in the disease-related processing mode in this embodiment, but the normal light image may be used. Further, medical images, such as a radiation image obtained from a radiographic device, a CT image obtained from computed tomography (CT), and a MRI image obtained from magnetic resonance imaging (MRI), may be used as an image, which is used in the disease-related processing mode, in addition to the special light image as an endoscopic image that is one of medical images. Furthermore, the processor device 16 to which the endoscope 12 is connected corresponds to an image processing device of the present invention and the disease-related processing mode is performed in the processor device 16, but the disease-related processing mode may be performed by other methods. For example, an external image processing device separate from the endoscope system 10 may be provided with the function of a disease-related processing section 66, a medical image may be input to the external image processing device to perform the disease-related processing mode, and the result of the disease-related processing mode may be displayed on an external display connected to the external image processing device.

The processor device 16 is electrically connected to the display 18 and the user interface 19. The display 18 outputs and displays the image of the object to be observed, information accessory to the image of the object to be observed, and the like. The user interface 19 has a function to receive an input operation, such as function settings. An external recording unit (not shown), which records images, image information, and the like, may be connected to the processor device 16. Further, the processor device 16 corresponds to the image processing device of the present invention.

Figure 2:
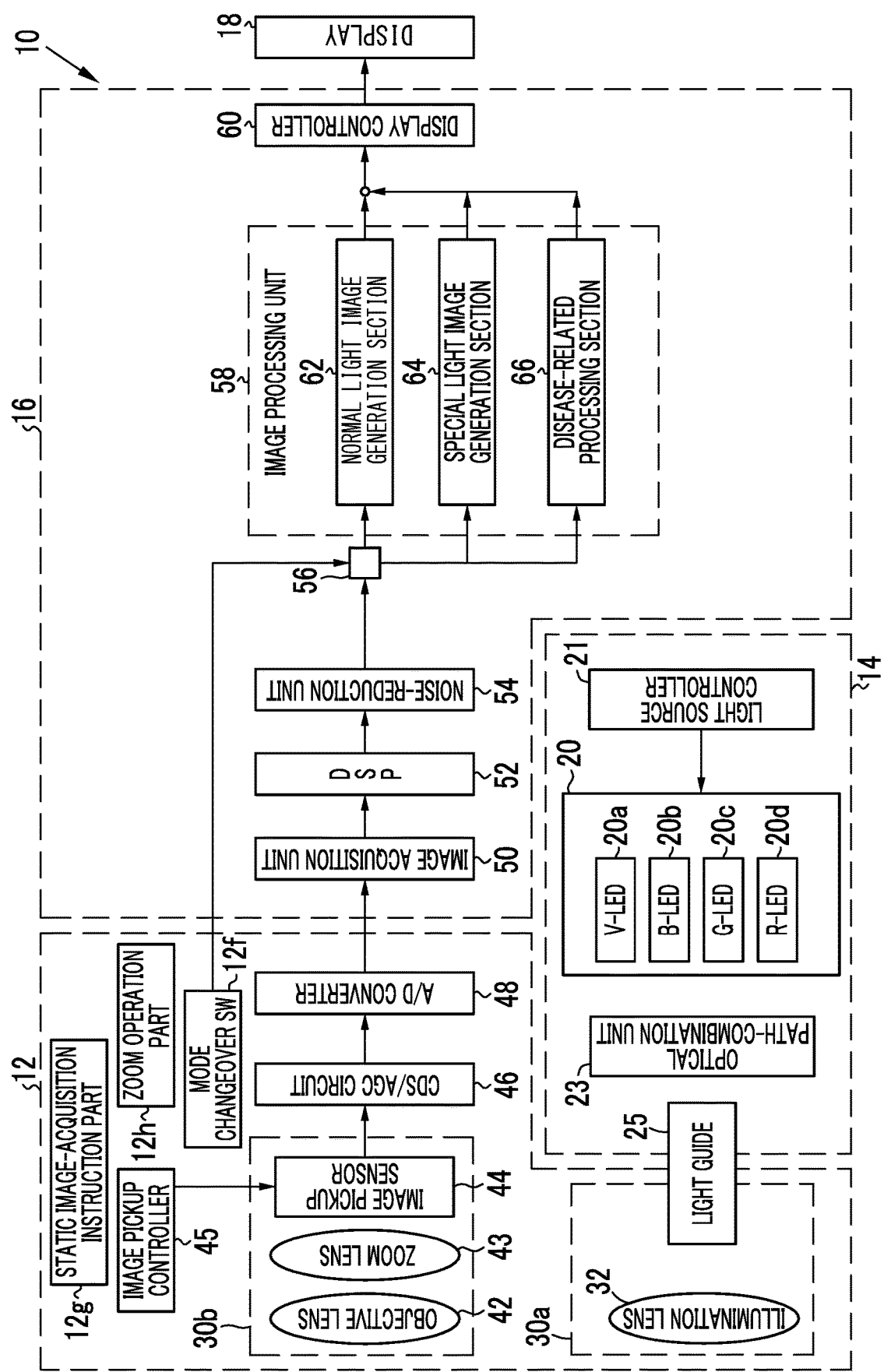
FIG. 2 is a block diagram showing the functions of the endoscope system according to a first embodiment.

In FIG. 2, the light source device 14 comprises a light source unit 20 and a light source controller 21 that controls the light source unit 20. The light source unit 20 includes, for example, a plurality of semiconductor light sources, turns on or off each of these semiconductor light sources, and emits illumination light, which illuminates the object to be observed, by controlling the amount of light from each semiconductor light source in a case where each semiconductor light source is turned on. In this embodiment, the light source unit 20 includes four color LEDs, that is, a violet light emitting diode (V-LED) 20a, a blue light emitting diode (B-LED) 20b, a green light emitting diode (G-LED) 20c, and a red light emitting diode (R-LED) 20d. In the light source device 14, programs related to various types of processing are incorporated into a program memory. The program incorporated into the program memory is executed by a central controller for a light source formed of a light source processor, so that the functions of the light source controller 21 are realized.

Figure 3:
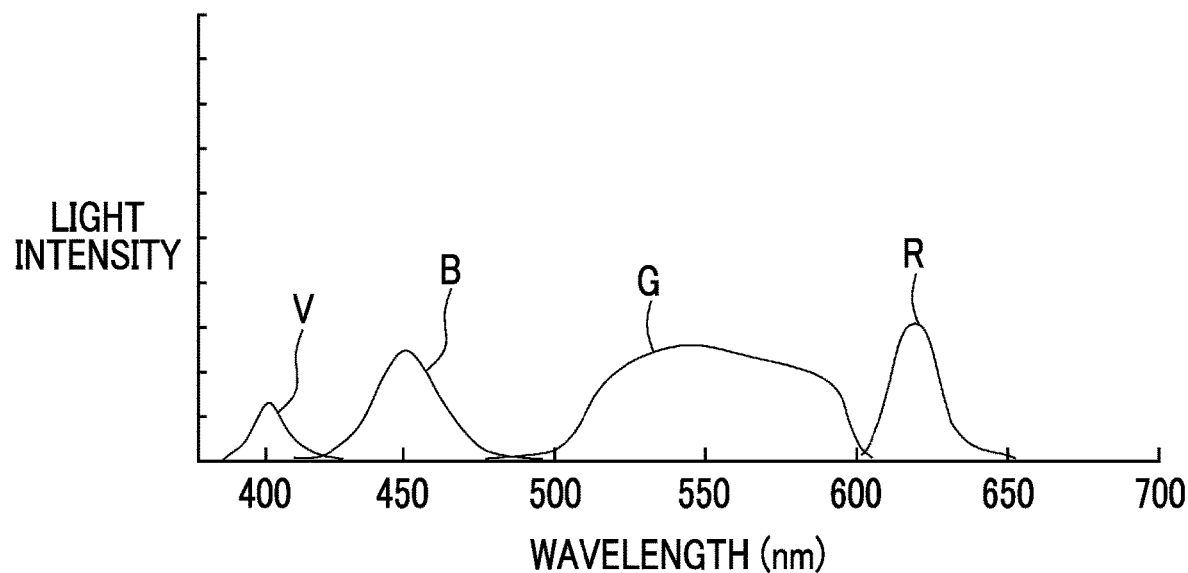
FIG. 3 is a graph showing the spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 450±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source controller 21 controls the V-LED 20a, the B-LED 20b, the G-LED 20c, and the R-LED 20d. Since the light source controller 21 independently controls each of the LEDs 20a to 20d, each of violet light V, blue light B, green light G, and red light R can be emitted independently while the amount of light is changed. Further, the light source controller 21 controls the respective LEDs 20a to 20d so that normal light of which the light amount ratio between violet light V, blue light B, green light G, and red light R is Vc:Bc:Gc:Rc is emitted in the normal light mode.

Furthermore, the light source controller 21 controls the respective LEDs 20a to 20d so that special light of which the light amount ratio between violet light V as narrow-band light having a short wavelength, blue light B, green light G, and red light R is Vs:Bs:Gs:Rs is emitted in the special light mode or the disease-related processing mode. In the disease-related processing mode, violet light V and green light G are mixed and emitted at a first light amount ratio as special light in order to obtain a blood vessel image in which a difference (the separability of a blood vessel depth) between an extremely superficial blood vessel positioned at a portion where a blood vessel depth (representing a distance (μm) from the surface of a mucous membrane in a depth direction orthogonal to the surface of the mucous membrane) is up to 50 μm and a superficial blood vessel positioned at a portion where a blood vessel depth is in the range of 50 μm to 200 μm is clarified. Further, in the disease-related processing mode, violet light V, green light G, and red light R are mixed and emitted at a second light amount ratio as special light in order to obtain a blood vessel image in which a difference between an extremely superficial blood vessel and a superficial blood vessel is clear. The details of the first light amount ratio and the second light amount ratio will be described later.

In this specification, the light amount ratio includes a case where the ratio of at least one semiconductor light source is 0 (zero). Accordingly, the light amount ratio includes a case where any one or two or more of the respective semiconductor light sources are not turned on. For example, even though only one semiconductor light source is turned on and the other three semiconductor light sources are not turned on as in a case where the light amount ratio between violet light V, blue light B, green light G, and red light R is 1:0:0:0, it is regarded that the light source unit 20 has a light amount ratio.

As shown in FIG. 2, light emitted from each of the LEDs 20a to 20d is incident on a light guide 25 through an optical path-combination unit 23 that is formed of mirrors, lenses, and the like. The light guide 25 is built in the endoscope 12 and a universal cord (a cord connecting the endoscope 12 to the light source device 14 and the processor device 16). The light guide 25 transmits light, which is emitted from the optical path-combination unit 23, to the distal end part 12d of the endoscope 12.

The distal end part 12d of the endoscope 12 is provided with an illumination optical system 30a and an image pickup optical system 30b. The illumination optical system 30a includes an illumination lens 32, and the object to be observed is irradiated with illumination light, which is transmitted by the light guide 25, through the illumination lens 32. The image pickup optical system 30b includes an objective lens 42 and an image pickup sensor 44. Light, which is emitted from the object to be observed since the object to be observed is irradiated with illumination light, is incident on the image pickup sensor 44 through the objective lens 42 and the zoom lens 43. Accordingly, the image of the object to be observed is formed on the image pickup sensor 44. The zoom lens 43 is a lens that is used to enlarge the object to be observed, and is moved between a telephoto end and a wide end in a case where the zoom operation part 12h is operated.

A charge coupled device (CCD) image pickup sensor or a complementary metal-oxide semiconductor (CMOS) image pickup sensor can be used as the image pickup sensor 44. Further, a complementary color image pickup sensor, which comprises complementary color filters corresponding to C (cyan), M (magenta), Y (yellow), and G (green), may be used instead of the primary color image pickup sensor 44. In a case where a complementary color image pickup sensor is used, image signals corresponding to four colors of C, M, Y, and G are output. Accordingly, the image signals corresponding to four colors of C, M, Y, and G are converted into image signals corresponding to three colors of R, G, and B by complementary color-primary color conversion, so that image signals corresponding to the same respective colors of R, G, and B as those of the image pickup sensor 44 can be obtained.

Figure 4:
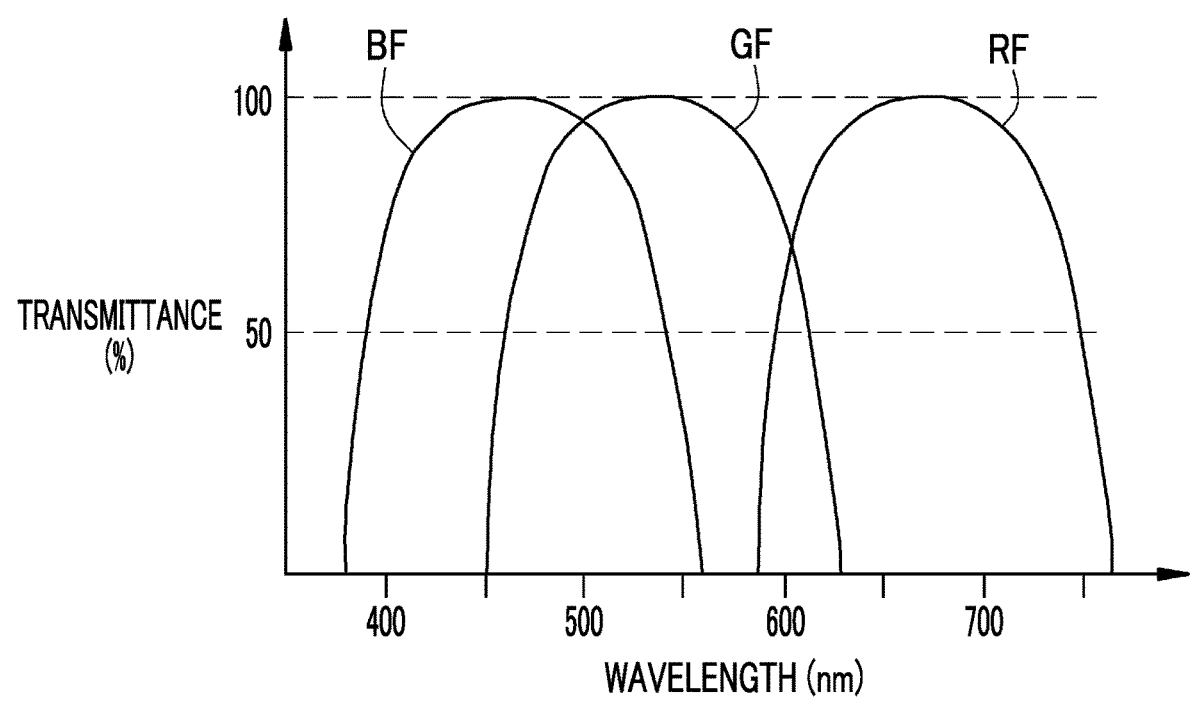
FIG. 4 is a graph showing the spectroscopic transmittance of each color filter of an image pickup sensor.

The image pickup sensor 44 is a primary color sensor, and comprises three types of pixels, that is, B pixels (blue pixel) including blue color filters, G pixels (green pixels) including green color filters, and R pixels (red pixels) including red color filters. As shown in FIG. 4, the blue color filter BF mainly transmits light of a blue light wavelength range, specifically, light of which the wavelength range is in the range of 380 to 560 nm. The transmittance of the blue color filter BF has a peak near a wavelength of 460 to 470 nm. The green color filter GF mainly transmits light of a green light wavelength range, specifically, light of which the wavelength range is in the range of 460 to 620 nm. The red color filter RF mainly transmits light of a red light wavelength range, specifically, light of which the wavelength range is in the range of 580 to 760 nm.

As shown in FIG. 2, the image pickup sensor 44 is driven and controlled by the image pickup controller 45. A control performed by the image pickup controller 45 varies depending on the respective modes. In the normal light mode, the image pickup controller 45 controls the image pickup sensor 44 so that the image pickup sensor 44 picks up the image of the object to be observed illuminated with normal light. Accordingly, blue images Bc are output from the B pixels of the image pickup sensor 44, green images Gc are output from the G pixels thereof, and red images Rc are output from the R pixels thereof.

In the special light mode or the disease-related processing mode, the image pickup controller 45 controls the image pickup sensor 44 so that the image pickup sensor 44 picks up the image of the object to be observed illuminated with special light. Accordingly, blue images Bs are output from the B pixels of the image pickup sensor 44, green images Gs are output from the G pixels thereof, and red images Rs are output from the R pixels thereof.

A correlated double sampling/automatic gain control (CDS/AGC) circuit 46 performs correlated double sampling (CDS) or automatic gain control (AGC) on analog image signals that are obtained from the image pickup sensor 44. The image signals, which have been transmitted through the CDS/AGC circuit 46, are converted into digital image signals by an analog/digital (A/D) converter 48. The digital image signals, which have been subjected to A/D conversion, are input to the processor device 16.

The processor device 16 comprises an image acquisition unit 50, a digital signal processor (DSP) 52, a noise-reduction unit 54, an image processing switching unit 56, an image processing unit 58, and a display controller 60. The image processing unit 58 comprises a normal light image generation section 62, a special light image generation section 64, and a disease-related processing section 66.

In the processor device 16, programs related to various types of processing are incorporated into a program memory. The programs incorporated into the program memory are executed by a central controller formed of an image control processor, so that the functions of the image acquisition unit 50, the noise-reduction unit 54, the image processing switching unit 56, the image processing unit 58, and the display controller 60 are realized.

The image acquisition unit 50 acquires the color image of an endoscopic image that is one of medical images input from the endoscope 12. The color image includes blue images, green images, and red images that are output from the B pixels, the G pixels, and the R pixels of the image pickup sensor 44. The acquired color image is transmitted to the DSP 52. The DSP 52 performs various types of signal processing, such as defect correction processing, offset processing, gain correction processing, matrix processing, gamma conversion processing, demosaicing processing, and YC conversion processing, on the received color image. Signals of defective pixels of the image pickup sensor 44 are corrected in the defect correction processing. Dark current components are removed from image signals subjected to the defect correction processing in the offset processing, so that an accurate zero level is set. The image signals, which have been subjected to the offset processing and correspond to each color, are multiplied by a specific gain in the gain correction processing, so that the signal level of the color image is adjusted. The matrix processing for improving color reproducibility is performed on the image signals that have been subjected to the gain correction processing and correspond to each color.

After that, the brightness or chroma saturation of the color image is adjusted by the gamma conversion processing. The demosaicing processing (also referred to as equalization processing or demosaicing) is performed on the color image subjected to the matrix processing, so that signals corresponding to colors missed in the respective pixels are generated by interpolation. All the pixels are made to have the signals corresponding to the respective colors of R, G, and B by the demosaicing processing. The DSP 52 performs the YC conversion processing on the color image subjected to the demosaicing processing, and outputs luminance signals Y, color difference signals Cb, and color difference signals Cr to the noise-reduction unit 54.

The noise-reduction unit 54 performs noise-reduction processing, which is performed using, for example, a moving average method, a median filtering method, or the like, on the color image that have been subjected to the demosaicing processing and the like by the DSP 56. The color image from which noise has been removed is input to the image processing switching unit 56.

The image processing switching unit 56 switches a destination, to which the image signals output from the noise-reduction unit 54 are to be transmitted, to any one of the normal light image generation section 62, the special light image generation section 64, or the disease-related processing section 66, depending on a set mode. Specifically, in a case where the endoscope system 10 is set to the normal light mode, the image signals output from the noise-reduction unit 54 are input to the normal light image generation section 62. In a case where the endoscope system 10 is set to the special light mode, the image signals output from the noise-reduction unit 54 are input to the special light image generation section 64. In a case where the endoscope system 10 is set to the disease-related processing mode, the image signals output from the noise-reduction unit 54 are input to the disease-related processing section 66.

The normal light image generation section 62 performs image processing for a normal light image on Rc image signals, Gc image signals, and Bc image signals that are input and correspond to one frame. The image processing for a normal light image includes color conversion processing, such as 3×3-matrix processing, gradation transformation processing, and three-dimensional look up table (LUT) processing, and structure enhancement processing, such as color enhancement processing and spatial frequency emphasis. The Rc image signals, the Gc image signals, and the Bc image signals subjected to the image processing for a normal light image are input to the display controller 60 as a normal light image.

The special light image generation section 64 performs image processing for a special light image on Rs image signals, Gs image signals, and Bs image signals that are input and correspond to one frame. The image processing for a special light image includes color conversion processing, such as 3×3-matrix processing, gradation transformation processing, and three-dimensional look up table (LUT) processing, and structure enhancement processing, such as color enhancement processing and spatial frequency emphasis. The Rs image signals, the Gs image signals, and the Bs image signals subjected to the image processing for a special light image are input to the display controller 60 as a special light image.

The disease-related processing section 66 performs processing, which is related to a disease, on the basis of the blood vessel image (an image in which a difference between an extremely superficial blood vessel and a superficial blood vessel is clarified) that is one of medical images. Specifically, the disease-related processing section 66 determines the stage of Barrett's esophagus as the processing related to a disease. Information about a determination result is input to the display controller 60. The details of the disease-related processing section 66 will be described later.

The display controller 60 performs a control to display the image, which is output from the image processing unit 58, on the display 18. Specifically, the display controller 60 converts the normal light image, the special light image, or the information about the determination result into video signals that allows the image or the information to be displayed on the display 18 in full color. The converted video signals are input to the display 18. Accordingly, the normal light image, the special light image, or the information about the determination result is displayed on the display 18.

Figure 5:
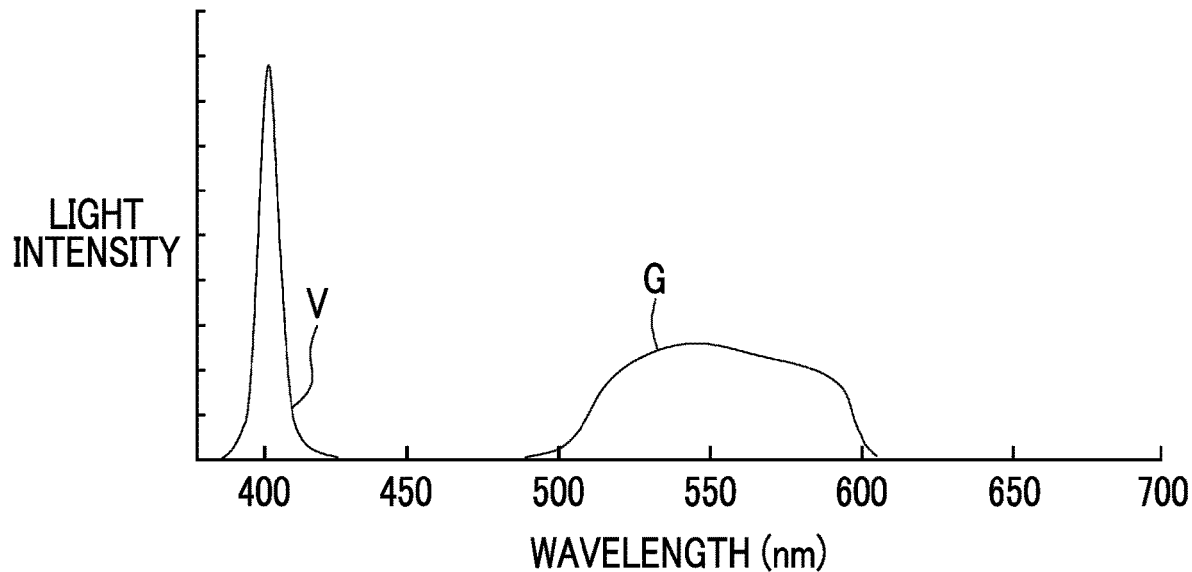
FIG. 5 is a graph showing an emission spectrum in a case where light is emitted at a first light amount ratio.

The first light amount ratio and the second light amount ratio required to obtain the blood vessel image in which a difference between an extremely superficial blood vessel and a superficial blood vessel is clear will be described. Vs and Gs are set to be larger than 0 and Bs and Rs are set to 0 with regard to the first light amount ratio as shown in FIG. 5, so that blue light B and red light R are not emitted and violet light V and green light G are mixed and emitted. The image of the object to be observed, to which light is emitted at the first light amount ratio, is picked up by the image pickup sensor 44, so that a color image of first mixed color light emission is obtained. The color image of first mixed color light emission includes blue images Bs that include components of violet light V and green images Gs that include components of green light G.

Figure 6:
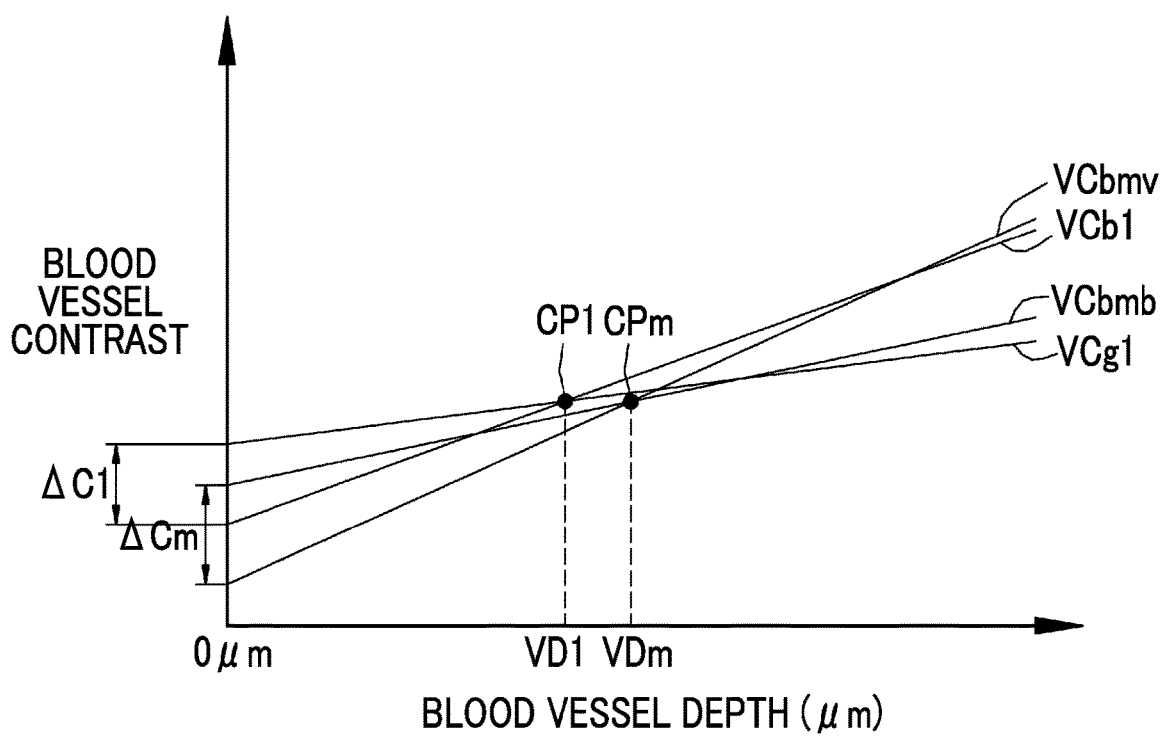
FIG. 6 is a graph showing a relationship between a blood vessel contrast and a blood vessel depth in the case of first mixed color light emission.

Since the color image of first mixed color light emission has the following characteristics with regard to a blood vessel contrast that shows contrast between a blood vessel and a non-blood vessel portion, such as a mucous membrane other than the blood vessel, it is possible to obtain a blood vessel image in which a difference between an extremely superficial blood vessel and a superficial blood vessel having blood vessel depths different from each other is clarified. As shown in FIG. 6, a contrast difference value $\Delta C1$ of first mixed color light emission between a blood vessel contrast VCb1 of a blue image Bs of first mixed color light emission and a blood vessel contrast VCg1 of a green image Gs of first mixed color light emission at a blood vessel depth of "0 μm" (specific depth) satisfies a first condition. In addition, a cross-point blood vessel depth VD1 of first mixed color light emission corresponding to a cross-point CP1 between the blood vessel contrast VCb1 of a blue image Bs of first mixed color light emission and the blood vessel contrast VCg1 of a green image Gs of first mixed color light emission satisfies a second condition. With regard to the specific depth, a blood vessel depth may exceed "0" and, for example, "10 μm" or less in addition to a blood vessel depth of "0 μm".

Figure 7:
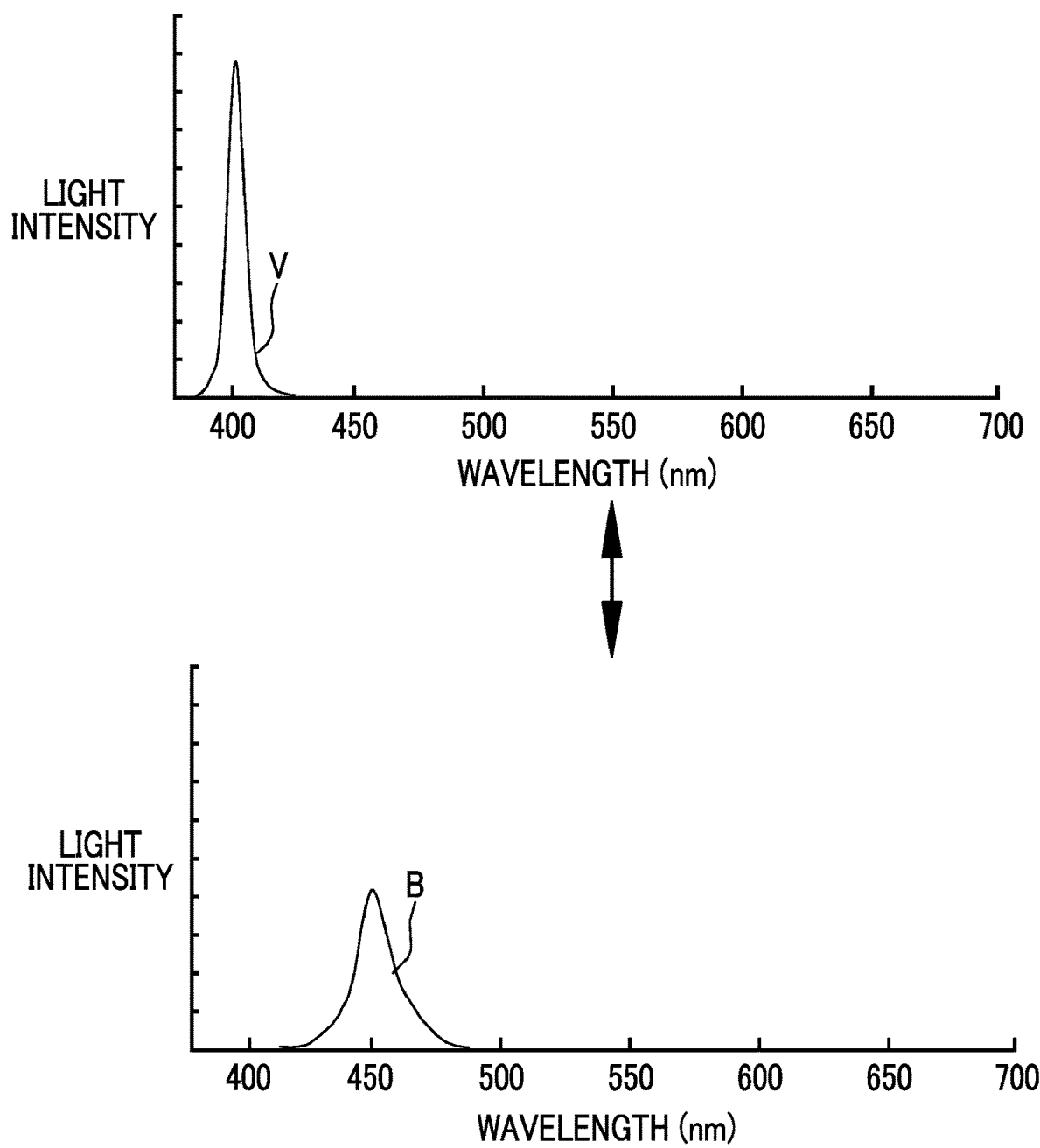
FIG. 7 is a diagram illustrating that violet light V and blue light B are alternately emitted.

The first condition and the second condition are determined through the comparison of blood vessel contrasts of monochromatic light emission that are obtained in cases where violet light V and blue light B are alternately emitted in a single color as shown in FIG. 7. Here, characteristics related to a blood vessel contrast of monochromatic light emission include a contrast difference value $\Delta Cm$ of monochromatic light emission between a blood vessel contrast VCbmv of a blue image Bs of monochromatic violet light emission that is obtained in a case where only violet light V is emitted at a blood vessel depth of "0 μm" (specific depth) and a blood vessel contrast VCbmb of a blue image Bs of monochromatic blue light emission that is obtained in a case where only blue light B is emitted. Further, the characteristics related to a blood vessel contrast of monochromatic light emission include a cross-point blood vessel depth VDm of monochromatic light emission corresponding to a cross-point CPm between the blood vessel contrast VCbmv of a blue image Bs of monochromatic violet light emission and the blood vessel contrast VCbmb of a blue image Bs of monochromatic blue light emission. In addition to satisfying the first condition and the second condition, it may be added that a change in the blood vessel contrast of first mixed color light emission satisfies a third condition. As the result of comparison of a change in the blood vessel contrast of first mixed color light emission and a change in the blood vessel contrast of monochromatic light emission, a case where a change in the blood vessel contrast of first mixed color light emission and a change in the blood vessel contrast of monochromatic light emission are similar to each other may be set as the third condition. Pattern matching and the like may be performed as processing related to comparison.

With regard to the first condition, the contrast difference value $\Delta C1$ of first mixed color light emission is in a first range determined on the basis of the contrast difference value $\Delta Cm$ of monochromatic light emission. The first range is, for example, preferably 50% or more of $\Delta Cm$ and more preferably 60% or more thereof. Specifically, since the contrast difference value $\Delta C1$ of first mixed color light emission of Example 1 is "0.085" in a case where the contrast difference value $\Delta Cm$ of monochromatic light emission is "0.147" as shown in the following examples, the contrast difference value $\Delta C1$ of first mixed color light emission of Example 1 is in the first range. With regard to the first condition, the contrast difference value $\Delta Cm$ of monochromatic light emission may be equal to or larger than a threshold value for a difference value in addition to a state where the contrast difference value $\Delta C1$ of first mixed color light emission of Example 1 is in the first range.

With regard to the second condition, a cross-point blood vessel depth VD1 of first mixed color light emission is in a second range determined on the basis of a cross-point blood vessel depth VDm of monochromatic light emission. The second range is, for example, preferably 1.4 times or less VDm. Specifically, since a cross-point blood vessel depth of first mixed color light emission of Example 1 is "55 μm" in a case where a cross-point blood vessel depth of monochromatic light emission is "60 μm" as shown in the following examples, the cross-point blood vessel depth of first mixed color light emission of Example 1 is in the second range.

Figure 8:
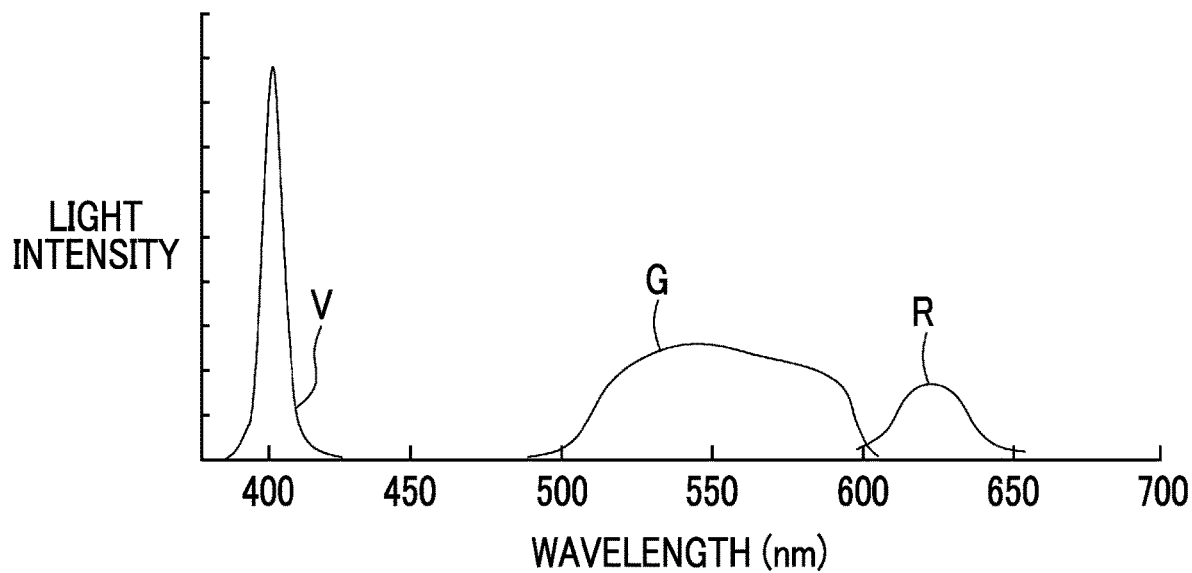
FIG. 8 is a graph showing an emission spectrum in a case where light is emitted at a second light amount ratio.

Vs, Gs, and Rs are set to be larger than 0 and a light amount ratio Bs is set to 0 with regard to the second light amount ratio as shown in FIG. 8, so that blue light B is not emitted and violet light V and green light G are mixed and emitted. The image of the object to be observed, to which light is emitted at the second light amount ratio, is picked up by the image pickup sensor 44, so that a color image of second mixed color light emission is obtained. The color image of second mixed color light emission includes blue images Bs that include components of violet light V and green images Gs that include components of green light G and components of red light R.

Figure 9:
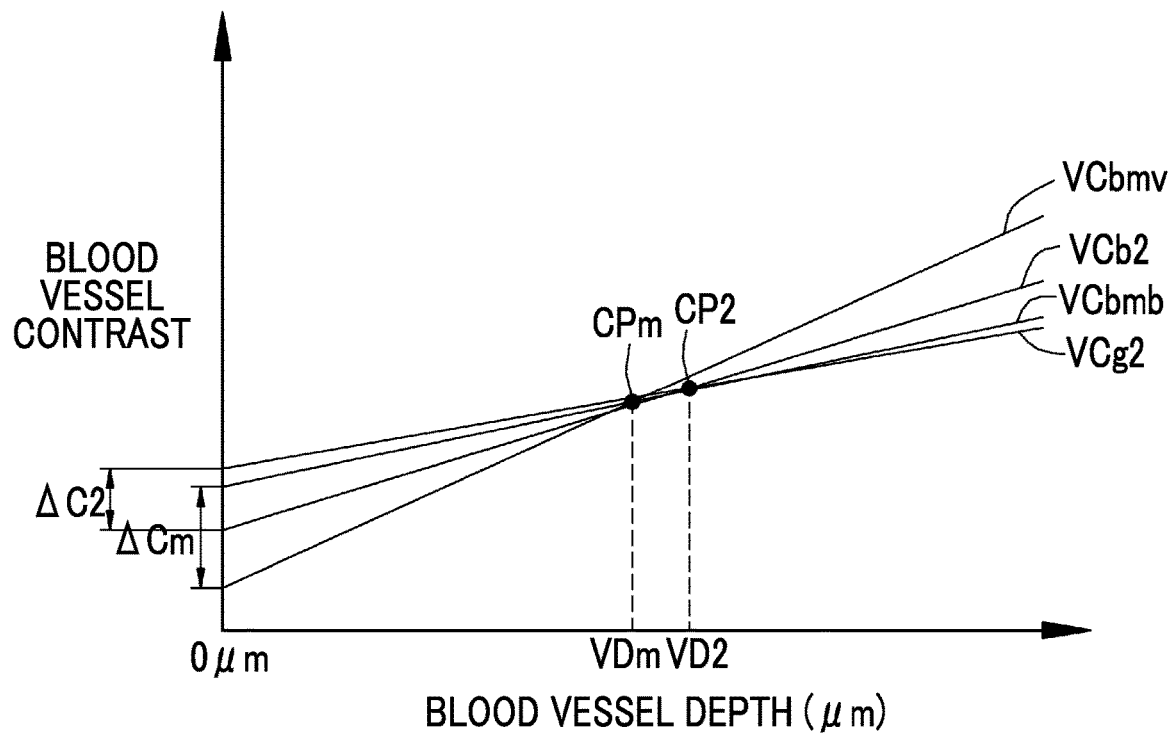
FIG. 9 is a graph showing a relationship between a blood vessel contrast and a blood vessel depth in the case of second mixed color light emission.

Since the color image of second mixed color light emission has the following characteristics with regard to a blood vessel contrast, it is possible to obtain a blood vessel image in which a difference between an extremely superficial blood vessel and a superficial blood vessel having blood vessel depths different from each other is clarified. As shown in FIG. 9, a contrast difference value $\Delta C2$ of second mixed color light emission between a blood vessel contrast VCb2 of a blue image Bs of second mixed color light emission and a blood vessel contrast VCg2 of a green image Gs of second mixed color light emission at a blood vessel depth of "0 μm" (specific depth) satisfies a second condition. In addition, a cross-point blood vessel depth VD2 of second mixed color light emission corresponding to a cross-point CP2 between the blood vessel contrast VCb2 of a blue image Bs of second mixed color light emission and the blood vessel contrast VCg2 of a green image Gs of second mixed color light emission satisfies a second condition. The first condition and the second condition in the case of second mixed color light emission may be the same as those in the case of first mixed color light emission, but may be different from those in the case of first mixed color light emission.

Figure 10:
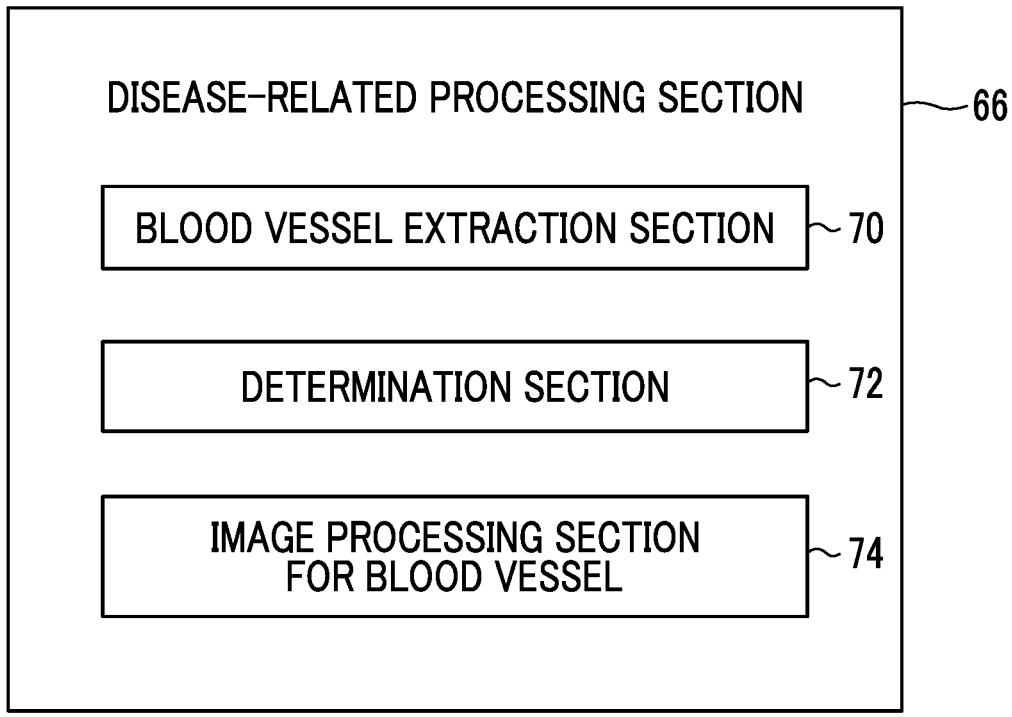
FIG. 10 is a block diagram showing the functions of a disease-related processing section.

The disease-related processing section 66 performs processing, which is related to a disease, on the basis of the color image of first mixed color light emission or second mixed color light emission as the special light image. Specifically, as shown in FIG. 10, the disease-related processing section 66 comprises: a blood vessel extraction section 70 that extracts extremely superficial blood vessels or superficial blood vessels from the color image of first mixed color light emission or second mixed color light emission; a determination section 72 that calculates the blood vessel density of extremely superficial blood vessels, ratios of the blood vessel density of the extremely superficial blood vessels and the blood vessel density of the superficial blood vessels, the distribution of these ratios, and the like on the basis of the extracted blood vessels and determines the stage of Barrett's esophagus; and an image processing section 74 for blood vessel that performs image processing for blood vessels, which increases a difference in visibility between a plurality of blood vessels having blood vessel depths different from each other, on the color image of second mixed color light emission.

The blood vessel extraction section 70 acquires an extracted blood vessel image on the basis of at least one of frequency characteristics or a luminance value obtained from the color image of first mixed color light emission or second mixed color light emission. A plurality of blood vessels having depths different from each other may be separated and extracted in the blood vessel extraction section 70. For example, the blood vessel extraction section 70 extracts blood vessel regions, in which the blood vessel contrast of a green image Gs of first mixed color light emission or second mixed color light emission is higher than the blood vessel contrast of a blue image Bs of first mixed color light emission or second mixed color light emission, as the extremely superficial blood vessels. On the other hand, the blood vessel extraction section 70 extracts blood vessel regions, in which the blood vessel contrast of a blue image Bs of first mixed color light emission or second mixed color light emission is higher than the blood vessel contrast of a green image Gs of first mixed color light emission or second mixed color light emission, as the superficial blood vessels that are present at a position deeper than the extremely superficial blood vessels. The extracted extremely superficial blood vessels and the extracted superficial blood vessels are combined with each other, so that the extracted blood vessel image is obtained.

The determination section 72 determines the stage of Barrett's esophagus using an index value (an index value related to the stage of a disease) that is obtained on the basis of the blood vessel density or dense area of the extremely superficial blood vessels or the blood vessel density or dense area of the superficial blood vessels in the extracted blood vessel image obtained by the blood vessel extraction section 70. It is preferable that ratios of the blood vessel density of the extremely superficial blood vessels and the blood vessel density of the superficial blood vessels are used as the index value. Specifically, the determination section 72 determines the stage of Barrett's esophagus as an early stage in a case where the index value is smaller than a threshold value, and determines the stage of Barrett's esophagus as a progression stage in a case where the index value is equal to or larger than the threshold value.

Figure 11:
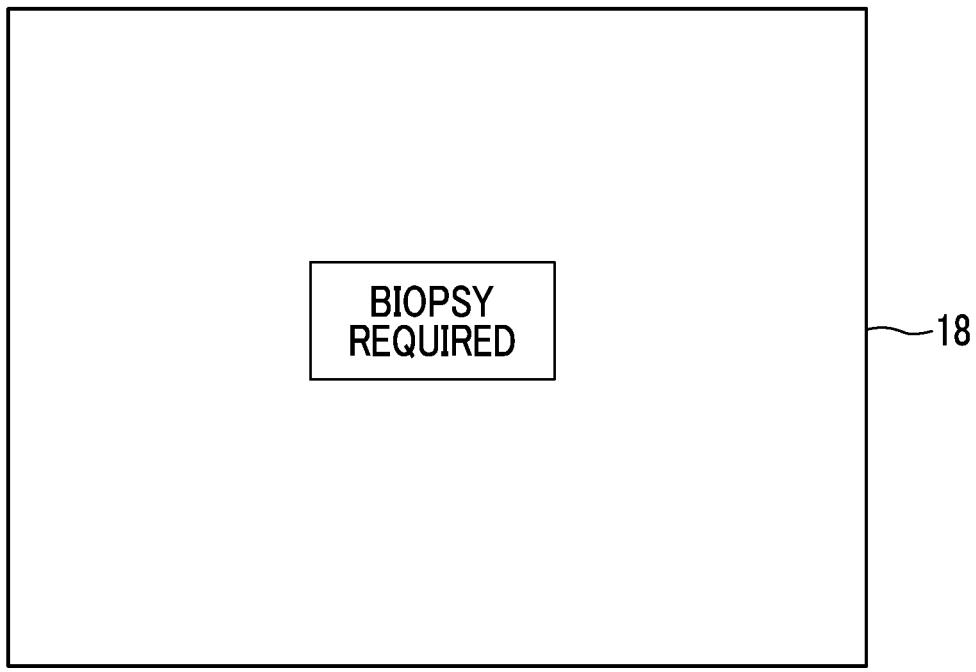
FIG. 11 is an image diagram of a display that displays information about determination.

Information about a determination made by the determination section 72 is displayed on the display 18, and is used for the determination of the stage of Barrett's esophagus that is made by a user. In a case where the stage of Barrett's esophagus is determined as a progression stage by the determination section 72, a message of "biopsy required" showing that a biopsy is required is displayed on the display 18 as shown in FIG. 11. In a case where information about a determination is displayed, it is preferable that a special light image used for a determination made by the determination section 72 and a heat map showing the distribution of the ratios of the blood vessel density of the extremely superficial blood vessels and the blood vessel density of the superficial blood vessels are superimposed and displayed.

The image processing section 74 for blood vessel performs image processing for blood vessels on the color image of second mixed color light emission to make a difference in visibility between the extremely superficial blood vessel and the superficial blood vessel of the color image of second mixed color light emission be close to that of the color image of first mixed color light emission. The reason why a difference between the extremely superficial blood vessel and the superficial blood vessel of the color image of second mixed color light emission can be improved by only the image processing for blood vessels as described above is that the contrast difference value $\Delta C2$ of second mixed color light emission is relatively large and color difference resolution is high. The image processing for blood vessels is gain processing or matrix processing that is set to improve a difference in visibility between the extremely superficial blood vessel and the superficial blood vessel. Further, the image processing for blood vessels may be performed on the color image of first mixed color light emission. In this case, it is preferable that the image processing for blood vessels is processing for increasing a difference in visibility between the extremely superficial blood vessel and the superficial blood vessel.

Figure 12:
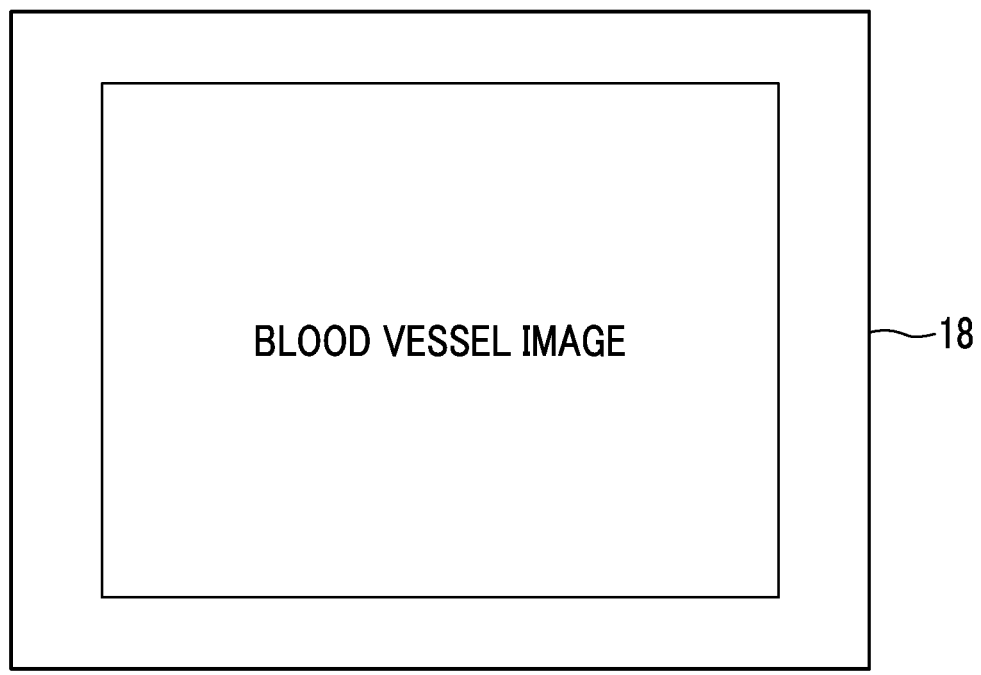
FIG. 12 is an image diagram of a display that displays a blood vessel image.

The color image of first mixed color light emission or second mixed color light emission has been used for the determination of the stage of Barrett's esophagus as described above, but may be displayed on the display 18 as a blood vessel image. In this case, the display controller 60 displays a blood vessel image, in which a difference between the extremely superficial blood vessel and the superficial blood vessel is clarified, on the display 18 as shown in FIG. 12 by assigning the blue images Bs of the color image of first mixed color light emission or second mixed color light emission to luminance signals Y, and assigning calculation images (difference images in a case where differences are used as calculation), which are based on the blue images Bs and the green images Gs of the color image of first mixed color light emission or second mixed color light emission, to color difference signals Cr and Cb.

Figure 13:
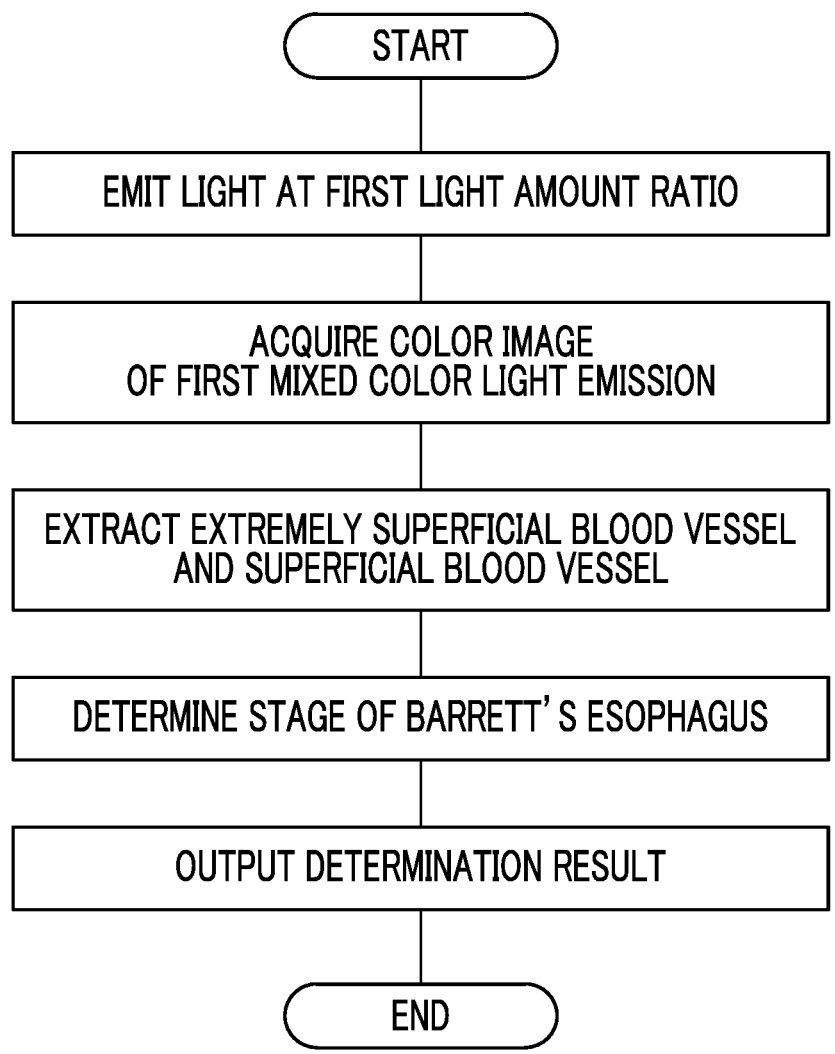
FIG. 13 is a flowchart showing a series of flows of a disease-related processing mode.

Next, a series of flows of the disease-related processing mode will be described with reference to a flowchart shown in FIG. 13. In a case where the endoscope system 10 is switched to the disease-related processing mode, violet light V and green light G are mixed and emitted at the first light amount ratio. The image of an object to be observed, to which light is emitted at the first light emission ratio, is picked up, so that a color image of first mixed color light emission is acquired. Since the color image of first mixed color light emission satisfies a first condition and a second condition related to a blood vessel contrast, a difference between an extremely superficial blood vessel and a superficial blood vessel is clarified. In a case where the color image of first mixed color light emission is used, the stage of, for example, Barrett's esophagus can be reliably determined.

The blood vessel extraction section 70 extracts extremely superficial blood vessels or superficial blood vessels on the basis of frequency characteristics or a luminance value obtained from the color image of first mixed color light emission. The determination section 72 determines the stage of Barrett's esophagus using an index value that is obtained on the basis of ratios of the blood vessel density of the extremely superficial blood vessels and the blood vessel density of the superficial blood vessels. Information about a determination made by the determination section 72 is displayed on the display 18.

EXAMPLES

In Examples and Comparative examples, specific examples in cases where the light amount ratio of illumination light is set to the first light amount ratio or the second light amount ratio and the first and second conditions are satisfied and specific example in cases where the first and second conditions are not satisfied are shown and the results (blood vessel images) of the cases of the specific examples are shown.

Example 1

As shown in FIG. 14, Vs:Bs:Gs:Rs was set to "1:0:0.45:0" as the first light amount ratio. Here, Vs:Bs:Gs:Rs is represented by the ratio of the amount (mw) of each color light emitted from each of the LEDs 20*a* to 20*d* through the distal end part 12*d* of the endoscope 12. In this case, blood vessel contrasts VCb1 (denoted by B0) and VCg1 (denoted by G0) of first mixed color light emission in a case where a blood vessel depth was "0 μm" were calculated using simulation processing, such as Monte Carlo simulation, and a contrast difference value ΔC1 of first mixed color light emission was obtained from these blood vessel contrasts. In addition, a cross-point blood vessel depth VDm of first mixed color light emission was calculated. As the simulation processing, the blood vessel contrasts are calculated on the basis of a calculation value that is obtained from the product of the first light amount ratio, the reflectance of an object to be observed (for example, the reflectance of the large intestine of a pig), and the transmittance of the image pickup sensor 44.

In order to check whether or not the first condition and the second condition are satisfied in Example 1, the other Examples 2 to 6, and Comparative examples 1 to 5, blood vessel contrasts VCbmv (denoted by B0*m*) and VCbmb (denoted by G0*m*) of monochromatic light emission in cases where violet light V and blue light B were emitted in a single color (monochromatic V, B light emission) and a blood vessel depth was "0 μm" were also calculated using simulation processing, such as Monte Carlo simulation. In addition, a cross-point blood vessel depth VDm of monochromatic light emission was calculated.

Example 2

Vs:Bs:Gs:Rs was set to "1:0:0.3:0" as the first light amount ratio. Others are the same as those of Example 1.

Example 3

Vs:Bs:Gs:Rs was set to "1:0:0.15:0" as the first light amount ratio. Others are the same as those of Example 1.

Example 4

Vs:Bs:Gs:Rs was set to "1:0:0.45:0.15" as the second light amount ratio. Then, blood vessel contrasts VCb2 (denoted by B0) and VCg2 (denoted by G0) of second mixed color light emission in a case where a blood vessel depth was "0 μm" were calculated, and a contrast difference value ΔC2 of second mixed color light emission was obtained from these blood vessel contrasts. In addition, a cross-point blood vessel depth VDm of second mixed color light emission was calculated.

Example 5

Vs:Bs:Gs:Rs was set to "1:0:0.3:0.1" as the second light amount ratio. Others are the same as those of Example 4.

Example 6

Vs:Bs:Gs:Rs was set to "1:0:0.15:0.05" as the second light amount ratio. Others are the same as those of Example 4.

Comparative Example 1

Figure 15:
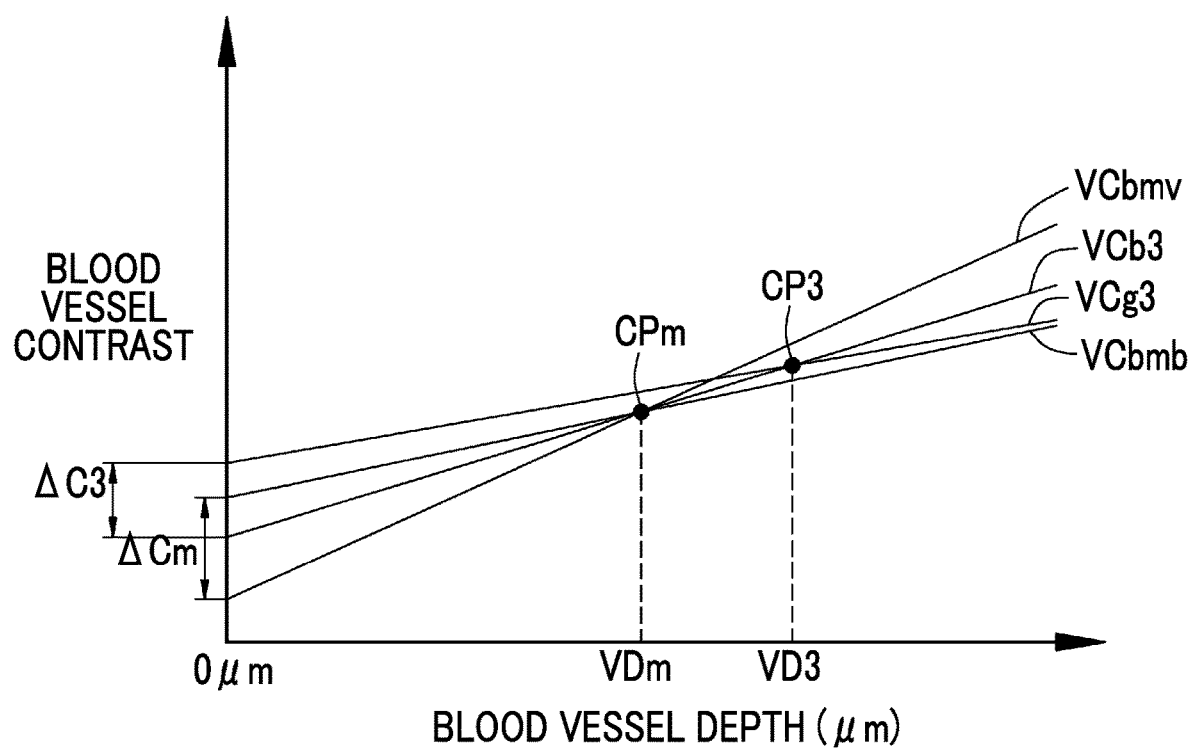
FIG. 15 is a graph showing a relationship between a blood vessel contrast and a blood vessel depth in the case of third mixed color light emission.

A light amount ratio Vs:Bs:Gs:Rs was set to "1:0:0.15:0.15", and mixed color light including at least violet light V, green light G, and red light R was emitted at a third light amount ratio. The image of an object to be observed is picked up at the third light amount ratio, so that a color image of third mixed color light emission is obtained. As shown in FIG. 15, characteristics related to a blood vessel contrast of third mixed color light emission include a contrast difference value ΔC3 of third mixed color light emission between a blood vessel contrast VCb3 of a blue image Bs of the color image of third mixed color light emission and a blood vessel contrast VCg3 of a green image Gs of the color image of third mixed color light emission at a blood vessel depth of "0 μm" (specific depth). Further, the characteristics related to a blood vessel contrast of third mixed color light emission include a cross-point blood vessel depth VD3 of third mixed color light emission corresponding to a cross-point CP3 between the blood vessel contrast VCb3 of a blue image Bs of third mixed color light emission and the blood vessel contrast VCg3 of a green image Gs of third mixed color light emission.

In Comparative example 1, blood vessel contrasts VCb3 (denoted by B0) and VCg3 (denoted by G0) of third mixed color light emission in a case where a blood vessel depth was "0 μm" were calculated using simulation processing, such as Monte Carlo simulation, and a contrast difference value ΔC3 of third mixed color light emission was obtained from these blood vessel contrasts. In addition, a cross-point blood vessel depth VD3 of third mixed color light emission was calculated. The simulation processing is the same as in Example 1.

Comparative Example 2

Vs:Bs:Gs:Rs was set to "1:0:0.15:0.1" as the third light amount ratio. Others are the same as those of Comparative example 1.

Comparative Example 3

Vs:Bs:Gs:Rs was set to "1:0.3:0.45:0.15" as the third light amount ratio. Others are the same as those of Comparative example 1.

Comparative Example 4

Vs:Bs:Gs:Rs was set to "1:0.2:0.3:0.1" as the third light amount ratio. Others are the same as those of Comparative example 1.

Comparative Example 5

Vs:Bs:Gs:Rs was set to "1:0.1:0.15:0.05" as the third light amount ratio. Others are the same as those of Comparative example 1.

[Results]

The contrast difference values and the cross-point blood vessel depths of Examples 1 to 6 and Comparative examples are shown in FIG. 14.

Figure 16:
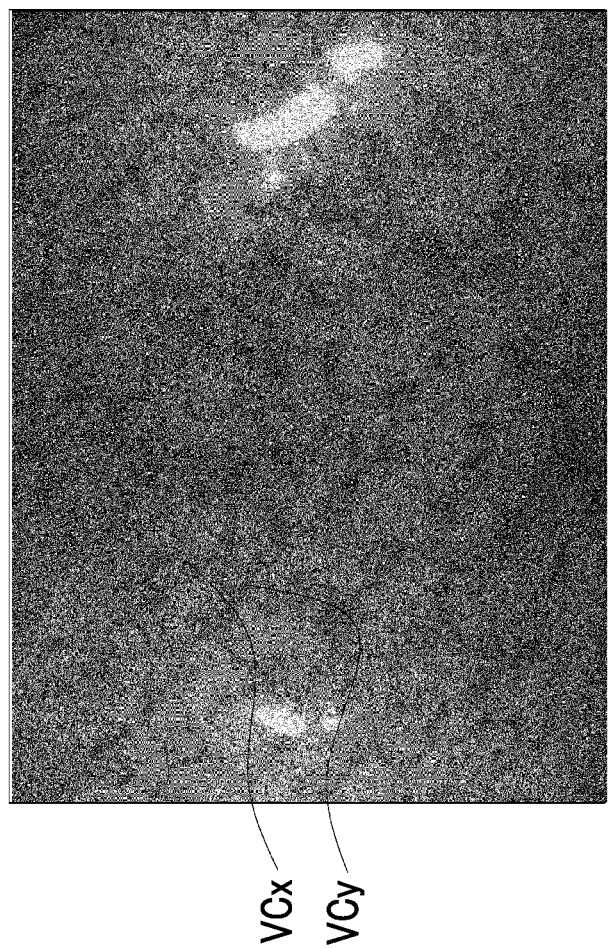
FIG. 16 is an image diagram showing a blood vessel image of Example 1.

In Example 1, the contrast difference value ΔC1 is "0.085" (G0−B0=0.346−0.261) and is in the first range (50% or more of the contrast difference value ΔCm ("0.147") of monochromatic light emission). Further, in Example 1, the cross-point blood vessel depth VD1 is "55 μm" and is in the second range (1.4 times or less the cross-point blood vessel depth VDm ("60 μm") of monochromatic light emission). Accordingly, both the first condition and the second condition are satisfied. For this reason, a difference between an extremely superficial blood vessel VCx and a superficial blood vessel VCy is clear in a blood vessel image of Example 1 (an image in which blue images Bs of first mixed color light emission are assigned to luminance signals Y and difference images of the blue images Bs and the green images of first mixed color light emission are assigned to color difference signals Cr and Cb) shown in FIG. 16 as in a blood vessel image shown in FIG. 17 that is obtained in the case of monochromatic light emission. As shown in FIG. 18, it is found that a difference between an extremely superficial blood vessel and a superficial blood vessel is clear even in a difference display image in which a difference image is represented by brightness.

In Example 2, the contrast difference value ΔC1 is "0.102" (G0−B0=0.338−0.236) and is in the first range (50% or more of the contrast difference value ΔCm ("0.147") of monochromatic light emission). Further, in Example 2, the cross-point blood vessel depth VD1 is "55 μm" and is in the second range (1.4 times or less the cross-point blood vessel depth VDm ("60 μm") of monochromatic light emission). Accordingly, both the first condition and the second condition are satisfied. For this reason, a blood vessel image in which a difference between an extremely superficial blood vessel and a superficial blood vessel is clear was obtained (not shown).

Figure 19:
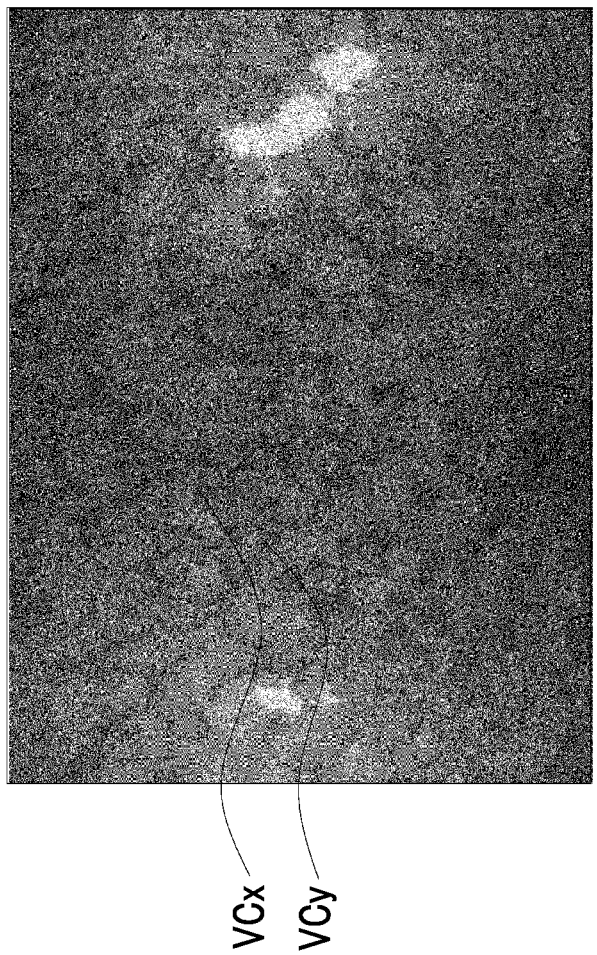
FIG. 19 is an image diagram showing a blood vessel image of Example 3.

In Example 3, the contrast difference value ΔC1 is "0.117" (G0−B0=0.317−0.200) and is in the first range (50% or more of the contrast difference value ΔCm ("0.147") of monochromatic light emission). Further, in Example 3, the cross-point blood vessel depth VD1 is "60 μm" and is in the second range (1.4 times or less the cross-point blood vessel depth VDm ("60 μm") of monochromatic light emission). Accordingly, both the first condition and the second condition are satisfied. For this reason, a difference between an extremely superficial blood vessel VCx and a superficial blood vessel VCy is clear in a blood vessel image of Example 3 shown in FIG. 19 as in the blood vessel image shown in FIG. 17 that is obtained in the case of monochromatic light emission.

In Example 4, the contrast difference value ΔC2 is "0.115" (G0−B0=0.393−0.278) and is in the first range (50% or more of the contrast difference value ΔCm ("0.147") of monochromatic light emission). Further, in Example 4, the cross-point blood vessel depth VD2 is "75 μm" and is in the second range (1.4 times or less the cross-point blood vessel depth VDm ("60 μm") of monochromatic light emission). Accordingly, both the first condition and the second condition are satisfied.

Figure 17:
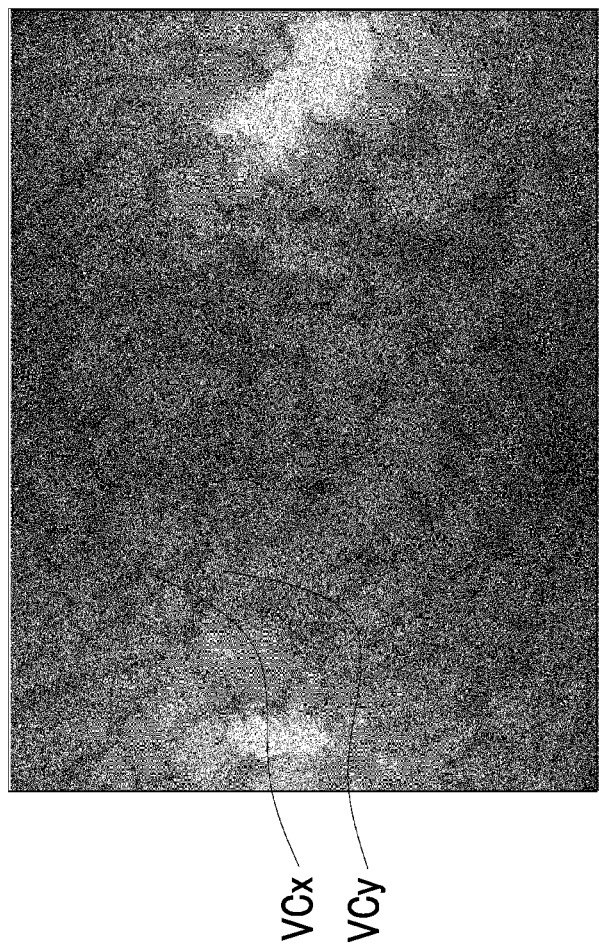
FIG. 17 is an image diagram showing a blood vessel image in the case of monochromatic light emission.
Figure 18:
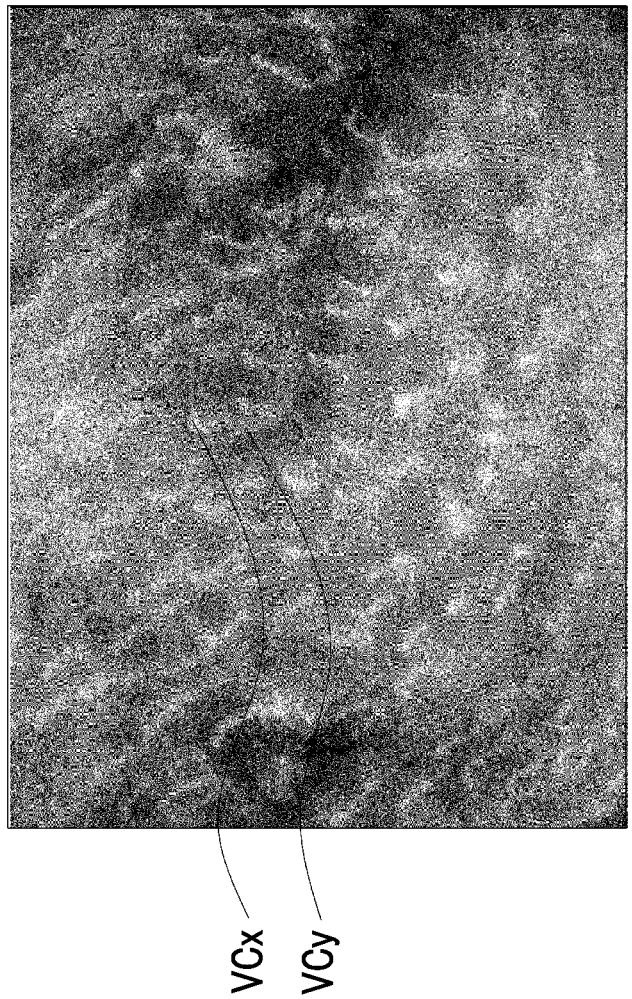
FIG. 18 is an image diagram showing a difference display image of Example 1.
Figure 20:
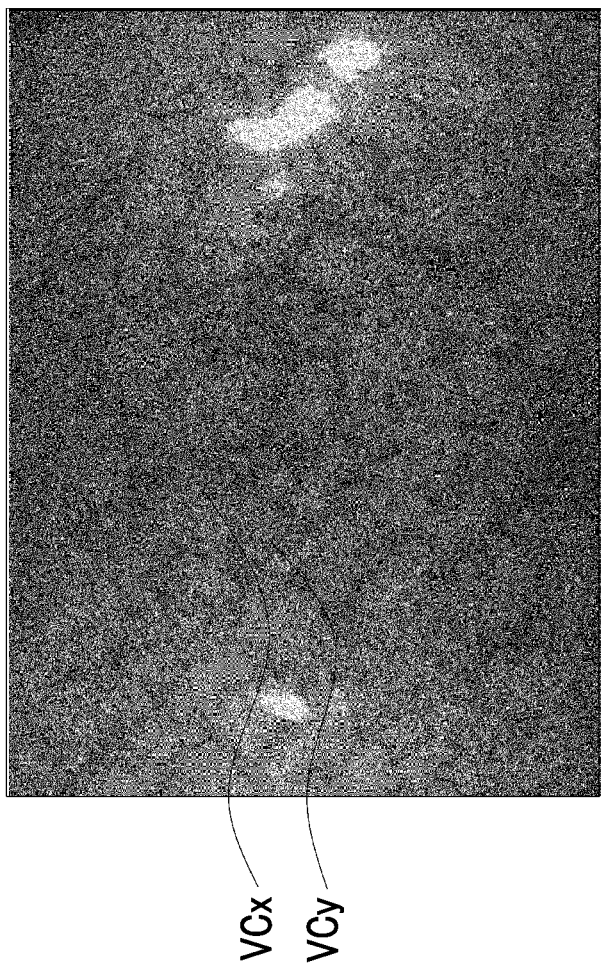
FIG. 20 is an image diagram showing a blood vessel image of Example 4.
Figure 21:
FIG. 21 is an image diagram showing a difference display image of Example 4.

For this reason, a difference between an extremely superficial blood vessel VCx and a superficial blood vessel VCy is clear in a blood vessel image of Example 4 shown in FIG. 20 as in the blood vessel image shown in FIG. 17 that is obtained in the case of monochromatic light emission. As shown in FIG. 21, it is found that a difference between an extremely superficial blood vessel and a superficial blood vessel is clear even in a difference display image in which difference images of the blue image Bs and the green image Gs of the color image of second mixed color light emission are represented by brightness. In Example 4 and the other Examples 5 and 6, it is found that the contrast difference value ΔC2 is larger than the contrast difference value ΔC1 and the cross-point blood vessel depth VD2 is larger than the cross-point blood vessel depth VD1 in a case where red light R is added to violet light V and green light G of Examples 1 to 3.

In Example 5, the contrast difference value ΔC2 is "0.134" (G0−B0=0.384−0.250) and is in the first range (50% or more of the contrast difference value ΔCm ("0.147") of monochromatic light emission). Further, in Example 5, the cross-point blood vessel depth VD2 is "75 μm" and is in the second range (1.4 times or less the cross-point blood vessel depth VDm ("60 μm") of monochromatic light emission). Accordingly, both the first condition and the second condition are satisfied. For this reason, a blood vessel image in which a difference between an extremely superficial blood vessel and a superficial blood vessel is clear was obtained (not shown).

Figure 22:
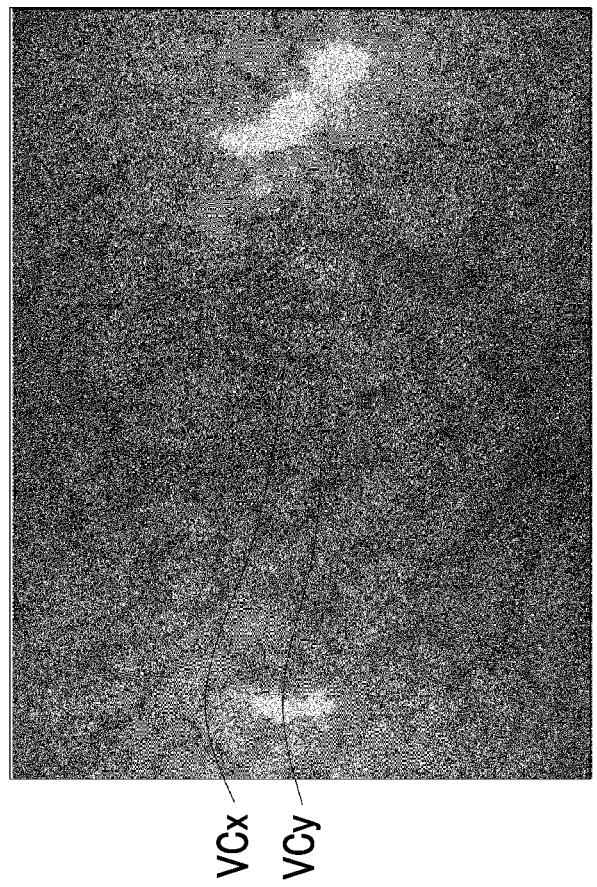
FIG. 22 is an image diagram showing a blood vessel image of Example 6.

In Example 6, the contrast difference value ΔC2 is "0.150" (G0−B0=0.359−0.209) and is in the first range (50% or more of the contrast difference value ΔCm ("0.147") of monochromatic light emission). Further, in Example 6, the cross-point blood vessel depth VD2 is "75 μm" and is in the second range (1.4 times or less the cross-point blood vessel depth VDm ("60 μm") of monochromatic light emission). Accordingly, both the first condition and the second condition are satisfied. For this reason, a difference between an extremely superficial blood vessel VCx and a superficial blood vessel VCy is clear in a blood vessel image of Example 6 shown in FIG. 22 as in the blood vessel image shown in FIG. 17 that is obtained in the case of monochromatic light emission.

Figure 23:
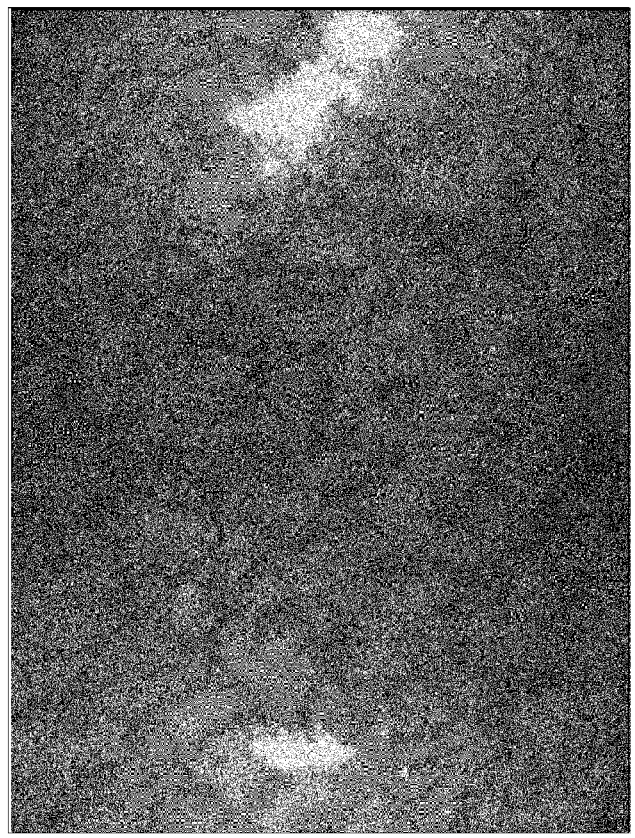
FIG. 23 is an image diagram showing a blood vessel image of Comparative example 1.

In Comparative example 1, the contrast difference value ΔC3 is "0.202" (G0−B0=0.359−0.209) and is in the first range (50% or more of the contrast difference value ΔCm ("0.147") of monochromatic light emission). On the other hand, in Comparative example 1, the cross-point blood vessel depth VD3 is "100 μm" and is out of the second range (1.4 times or less the cross-point blood vessel depth VDm ("60 μm") of monochromatic light emission). Accordingly, the first condition is satisfied but the second condition is not satisfied. For this reason, a difference between an extremely superficial blood vessel VCx and a superficial blood vessel VCy is not clear in a blood vessel image of Comparative example 1 shown in FIG. 23 significantly unlike the blood vessel image shown in FIG. 17 that is obtained in the case of monochromatic light emission.

In Comparative example 2, the contrast difference value ΔC3 is "0.178" (G0−B0=0.396−0.218) and is in the first range (50% or more of the contrast difference value ΔCm ("0.147") of monochromatic light emission). On the other hand, in Comparative example 2, the cross-point blood vessel depth VD3 is "100 μm" and is out of the second range (1.4 times or less the cross-point blood vessel depth VDm ("60 μm") of monochromatic light emission). Accordingly, the first condition is satisfied but the second condition is not satisfied. For this reason, a blood vessel image in which a difference between an extremely superficial blood vessel and a superficial blood vessel is clear could not be obtained (not shown).

In Comparative example 3, the contrast difference value ΔC3 is "0.099" (G0−B0=0.383−0.284) and is in the first range (50% or more of the contrast difference value ΔCm ("0.147") of monochromatic light emission). On the other hand, in Comparative example 3, the cross-point blood vessel depth VD3 is "85 μm" and is out of the second range (1.4 times or less the cross-point blood vessel depth VDm ("60 μm") of monochromatic light emission). Accordingly, the first condition is satisfied but the second condition is not satisfied. For this reason, a blood vessel image in which a difference between an extremely superficial blood vessel and a superficial blood vessel is clear could not be obtained (not shown).

In Comparative example 4, the contrast difference value ΔC3 is "0.110" (G0−B0=0.375−0.265) and is in the first range (50% or more of the contrast difference value ΔCm ("0.147") of monochromatic light emission). On the other hand, in Comparative example 4, the cross-point blood vessel depth VD3 is "85 μm" and is out of the second range (1.4 times or less the cross-point blood vessel depth VDm ("60 μm") of monochromatic light emission). Accordingly, the first condition is satisfied but the second condition is not satisfied. For this reason, a blood vessel image in which a difference between an extremely superficial blood vessel and a superficial blood vessel is clear could not be obtained (not shown).

In Comparative example 5, the contrast difference value ΔC3 is "0.123" (G0−B0=0.354−0.231) and is in the first range (50% or more of the contrast difference value ΔCm ("0.147") of monochromatic light emission). On the other hand, in Comparative example 5, the cross-point blood vessel depth VD3 is "85 μm" and is out of the second range (1.4 times or less the cross-point blood vessel depth VDm ("60 μm") of monochromatic light emission). Accordingly, the first condition is satisfied but the second condition is not satisfied. For this reason, a blood vessel image in which a difference between an extremely superficial blood vessel and a superficial blood vessel is clear could not be obtained (not shown).

From the results of Examples 1 to 6 and Comparative examples 1 to 5, it is found that it is advantageous to set a light amount ratio, at which a cross-point blood vessel depth is made close to the cross-point blood vessel depth VDm of monochromatic light emission by adding green light G to violet light V serving as a base, as the first light amount ratio. Further, it is found that it is advantageous to set a light amount ratio, at which red light R is added to violet light V and green light G so that a contrast difference value is as large as possible while a cross-point blood vessel depth is maintained at a value as close as possible to the cross-point blood vessel depth VDm of monochromatic light emission, as the second light amount ratio.

The hardware structures of the processing units, which are included in the image processing unit 58 and execute various types of processing in the above-mentioned embodiment, such as the normal light image generation section 62, the special light image generation section 64, the disease-related processing section 66, the blood vessel extraction section 70, the determination section 72, and the image processing section 74 for blood vessel, are various processors to be described below. The various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit that is a processor having circuit configuration designed exclusively to perform various types of processing; and the like.

One processing unit may be formed of one of these various processors, or may be formed of a combination of two or more same type or different types of processors (for example, a plurality of FPGAs, or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by a system-on-chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined. Further, the hardware structure of the storage unit is a storage device, such as a hard disc drive (HDD) or a solid state drive (SSD).

The present invention can be embodied by another aspect according to the following additional claim 1.

[Additional Claim 1]

An endoscope system comprising:

a light source unit that emits violet light and green light;

a light source controller that allows the violet light and the green light to be independently emitted and allows the violet light and the green light to be mixed and emitted at a first light amount ratio; and an image acquisition unit acquiring a color image of first mixed color light emission that is obtained from image pickup of an object to be observed, to which the violet light and the green light are emitted at the first light amount ratio, and includes a blue image including a component of the violet light and a green image including a component of the green light, wherein a contrast difference value of first mixed color light emission between a blood vessel contrast of the blue image of the first mixed color light emission and a blood vessel contrast of the green image of the first mixed color light emission at a specific blood vessel depth is in a first range with respect to a contrast difference value of monochromatic light emission between a blood vessel contrast of a blue image of monochromatic violet light emission, which is obtained in a case where only the violet light is emitted at the specific blood vessel depth, and a blood vessel contrast of a blue image of monochromatic blue light emission which is obtained in a case where only the blue light is emitted, and a cross-point blood vessel depth of first mixed color light emission corresponding to a cross-point between the blood vessel contrast of the blue image of the first mixed color light emission and the blood vessel contrast of the green image of the first mixed color light emission is in a second range with respect to a cross-point blood vessel depth of monochromatic light emission corresponding to a cross-point between a blood vessel contrast of a blue image of monochromatic violet light emission, which is obtained in a case where only the violet light is emitted, and a blood vessel contrast of a blue image of monochromatic blue light emission which is obtained in a case where only blue light is emitted.

EXPLANATION OF REFERENCES

10: endoscope system
12: endoscope

12a: insertion part
12b: operation part
12c: bendable part
12d: distal end part
12e: angle knob
12f: mode changeover switch
12g: static image-acquisition instruction part
12h: zoom operation part
14: light source device
16: processor device
18: display
19: user interface
20: light source unit
20a: V-LED
20b: B-LED
20c: G-LED
20d: R-LED
21: light source controller
23: optical path-combination unit
25: light guide
30a: illumination optical system
30b: image pickup optical system
32: illumination lens
42: objective lens
43: zoom lens
44: image pickup sensor
45: image pickup controller
46: CDS/AGC circuit
48: A/D converter
50: image acquisition unit
52: DSP
54: noise-reduction unit
56: image processing switching unit
58: image processing unit
60: display controller
62: normal light image generation section
64: special light image generation section
66: disease-related processing section
70: blood vessel extraction section
72: determination section
74: image processing section for blood vessel
CP1: cross-point of first mixed color light emission
CP2: cross-point of second mixed color light emission
CP3: cross-point of third mixed color light emission
CPm: cross-point of monochromatic light emission
VCb1: blood vessel contrast of blue image of first mixed color light emission
VCb2: blood vessel contrast of blue image of second mixed color light emission
VCb3: blood vessel contrast of blue image of third mixed color light emission
VCg1: blood vessel contrast of green image of first mixed color light emission
VCg2: blood vessel contrast of green image of second mixed color light emission
VCg3: blood vessel contrast of green image of third mixed color light emission
VCbmv: blood vessel contrast of blue image of monochromatic violet light emission
VCbmb: blood vessel contrast of blue image of monochromatic blue light emission
ΔC1: contrast difference value of first mixed color light emission
ΔC2: contrast difference value of second mixed color light emission
ΔC3: contrast difference value of third mixed color light emission
ΔCm: contrast difference value of monochromatic light emission
VD1: cross-point blood vessel depth of first mixed color light emission
VD2: cross-point blood vessel depth of second mixed color light emission
VD3: cross-point blood vessel depth of third mixed color light emission
VDm: cross-point blood vessel depth of monochromatic light emission

What is claimed is:

1. An endoscope system comprising:
a light source that emits violet light and green light;
a light source controller configured to allow the violet light and the green light to be independently emitted and allow the violet light and the green light to be mixed and emitted as a first mixed color light emission at a first light amount ratio; and
a processor device configured to acquire a color image of the first mixed color light emission that is obtained from image pickup of an object to be observed, and which includes a blue image signal that includes a component of the violet light and a green image signal that includes a component of the green light,
wherein a contrast difference value of the first mixed color light emission between a blood vessel contrast of the blue image signal of the first mixed color light emission and a blood vessel contrast of the green image signal of the first mixed color light emission at a specific blood vessel depth satisfies a first condition, and
a cross-point blood vessel depth of the first mixed color light emission corresponding to a cross-point between the blood vessel contrast of the blue image signal of the first mixed color light emission and the blood vessel contrast of the green image signal of the first mixed color light emission satisfies a second condition, wherein
the first condition is that the contrast difference value of the first mixed color light emission is in a first range determined on the basis of a contrast difference value of a monochromatic light emission between a blood vessel contrast of a blue image signal of a monochromatic violet light emission, which is obtained in a case where only the violet light is emitted at the specific blood vessel depth, and a blood vessel contrast of a blue image signal of a monochromatic blue light emission which is obtained in a case where only blue light is emitted, and
the second condition is that the cross-point blood vessel depth of the first mixed color light emission is in a second range determined on the basis of a cross-point blood vessel depth of the monochromatic light emission corresponding to a cross-point between a blood vessel contrast of a blue image signal of the monochromatic violet light emission, which is obtained in a case where only the violet light is emitted, and a blood vessel contrast of a blue image signal of the monochromatic blue light emission which is obtained in a case where only blue light is emitted.

2. The endoscope system according to claim 1,
wherein the processor device is further configured to perform image processing for blood vessels, which increases a difference in visibility between a plurality of blood vessels having blood vessel depths different from each other, on the color image of the first mixed color light emission.

3. The endoscope system according to claim 1,
wherein the processor device is further configured to calculate an index value related to a stage of a disease or determines the stage of the disease on the basis of the color image.

4. The endoscope system according to claim 1,
wherein the processor device is further configured to display a blood vessel image, which is obtained in a case where the blue image signal is assigned to luminance signals and calculation images based on the blue image signal and the green image signal are assigned to color difference signals, on a display.

5. The endoscope system according to claim 1,
wherein the processor device is further configured to separate and extract a plurality of blood vessels, which have blood vessel depths different from each other, on the basis of the color image.

6. The endoscope system according to claim 1,
wherein a central wavelength of the violet light includes a wavelength of 405 nm and a wavelength range of the green light includes a wavelength of 480 to 600 nm.

7. An endoscope system comprising:
a light source that emits violet light, green light, and red light;
a light source controller configured to allow the violet light, the green light, and the red light to be independently emitted and allow the violet light, the green light, and the red light to be mixed and emitted as a second mixed color light emission at a second light amount ratio; and
a processor device configured to acquire a color image of the second mixed color light emission that is obtained from image pickup of an object to be observed, and which includes a blue image signal that includes a component of the violet light and a green image signal that includes components of the green light and the red light,
wherein a contrast difference value of the second mixed color light emission between a blood vessel contrast of the blue image signal of the second mixed color light emission and a blood vessel contrast of the green image signal of the second mixed color light emission at a specific blood vessel depth satisfies a first condition, and
a cross-point blood vessel depth of second mixed color light emission corresponding to a cross-point between the blood vessel contrast of the blue image signal of the second mixed color light emission and the blood vessel contrast of the green image signal of the second mixed color light emission satisfies a second condition, wherein
the first condition is that the contrast difference value of the first mixed color light emission is in a first range determined on the basis of a contrast difference value of a monochromatic light emission between a blood vessel contrast of a blue image signal of a monochromatic violet light emission, which is obtained in a case where only the violet light is emitted at the specific blood vessel depth, and a blood vessel contrast of a blue image signal of a monochromatic blue light emission which is obtained in a case where only blue light is emitted, and
the second condition is that the cross-point blood vessel depth of the first mixed color light emission is in a second range determined on the basis of a cross-point blood vessel depth of the monochromatic light emission corresponding to a cross-point between a blood vessel contrast of a blue image signal of the monochromatic violet light emission, which is obtained in a case where only the violet light is emitted, and a blood vessel contrast of a blue image signal of the monochromatic blue light emission which is obtained in a case where only blue light is emitted.

8. The endoscope system according to claim 7,
wherein the processor device is further configured to perform image processing for blood vessels, which increases a difference in visibility between a plurality of blood vessels having blood vessel depths different from each other, on the color image of the second mixed color light emission.

9. The endoscope system according to claim 7,
wherein the processor device is further configured to calculate an index value related to a stage of a disease or determines the stage of the disease on the basis of the color image.

10. The endoscope system according to claim 7,
wherein the processor device is further configured to display a blood vessel image, which is obtained in a case where the blue image signal is assigned to luminance signals and calculation images based on the blue image signal and the green image signal are assigned to color difference signals, on a display.

11. The endoscope system according to claim 7,
wherein the processor device is further configured to separate and extract a plurality of blood vessels, which have blood vessel depths different from each other, on the basis of the color image.

12. The endoscope system according to claim 7,
wherein a central wavelength of the violet light includes a wavelength of 405 nm, a wavelength range of the green light includes a wavelength of 480 to 600 nm, and a central wavelength of the red light includes a wavelength of 620 to 630 nm.

13. A method of operating an endoscope system, the method comprising:
a step of causing a light source controller, which is configured to control a light source that emits violet light and green light, to allow the violet light and the green light to be independently emitted and to allow the violet light and the green light to be mixed and emitted as a first mixed color light emission at a first light amount ratio; and
a step of acquiring a color image of the first mixed color light emission that is obtained from image pickup of an object to be observed, and which includes a blue image signal that includes a component of the violet light and a green image signal that includes a component of the green light,
wherein a contrast difference value of the first mixed color light emission between a blood vessel contrast of the blue image signal of the first mixed color light emission and a blood vessel contrast of the green image signal of the first mixed color light emission at a specific blood vessel depth satisfies a first condition, and
a cross-point blood vessel depth of the first mixed color light emission corresponding to a cross-point between the blood vessel contrast of the blue image signal of the first mixed color light emission and the blood vessel contrast of the green image signal of the first mixed color light emission satisfies a second condition, wherein
the first condition is that the contrast difference value of the first mixed color light emission is in a first range determined on the basis of a contrast difference value of a monochromatic light emission between a blood vessel contrast of a blue image signal of a monochromatic violet light emission, which is obtained in a case where only the violet light is emitted at the specific blood vessel depth, and a blood vessel contrast of a blue image signal of a monochromatic blue light emission which is obtained in a case where only blue light is emitted, and the second condition is that the cross-point blood vessel depth of the first mixed color light emission is in a second range determined on the basis of a cross-point blood vessel depth of the monochromatic light emission corresponding to a cross-point between a blood vessel contrast of a blue image signal of the monochromatic violet light emission, which is obtained in a case where only the violet light is emitted, and a blood vessel contrast of a blue image signal of the monochromatic blue light emission which is obtained in a case where only blue light is emitted.

* * * * *